United States Patent
He et al.

(10) Patent No.: US 8,809,314 B1
(45) Date of Patent: Aug. 19, 2014

(54) CEPHALOSPORIN COMPOUND

(71) Applicant: Cubist Pharmaceuticals, Inc., Lexington, MA (US)

(72) Inventors: Yong He, Bedford, MA (US); Yu Gui Gu, Acton, MA (US); Ning Yin, Lexington, MA (US); Dong Zou, Concord, MA (US); Andre Lee Pearson, Brooklyn, NY (US)

(73) Assignee: Cubist Pharmacueticals, Inc., Lexington, MA (US)

( * ) Notice: Subject to any disclaimer, the term of this patent is extended or adjusted under 35 U.S.C. 154(b) by 0 days.

(21) Appl. No.: 14/020,230

(22) Filed: Sep. 6, 2013

Related U.S. Application Data

(60) Provisional application No. 61/698,241, filed on Sep. 7, 2012.

(51) Int. Cl.
   *A61K 31/545* (2006.01)
   *C07D 501/00* (2006.01)
   *C07D 501/14* (2006.01)
   *C07D 501/18* (2006.01)

(52) U.S. Cl.
   CPC .................... *C07D 501/18* (2013.01)
   USPC ............................ 514/203; 514/204; 540/225

(58) Field of Classification Search
   None
   See application file for complete search history.

(56) References Cited

U.S. PATENT DOCUMENTS

| | | | |
|---|---|---|---|
| 4,200,575 A | 4/1980 | Numata et al. |
| 4,246,405 A | 1/1981 | Takaya et al. |
| 4,255,431 A | 3/1981 | Junggren et al. |
| 4,264,597 A | 4/1981 | Hashimoto et al. |
| 4,267,176 A | 5/1981 | Kamiya et al. |
| 4,268,509 A | 5/1981 | Teraji et al. |
| 4,284,631 A | 8/1981 | Takaya et al. |
| 4,291,031 A | 9/1981 | Takaya et al. |
| 4,298,529 A | 11/1981 | Ueda et al. |
| 4,299,829 A | 11/1981 | Kamiya et al. |
| 4,305,937 A | 12/1981 | Kamiya et al. |
| 4,327,093 A | 4/1982 | Ueda et al. |
| 4,331,665 A | 5/1982 | Teraji et al. |
| 4,332,798 A | 6/1982 | Teraji et al. |
| 4,332,800 A | 6/1982 | Teraji et al. |
| 4,336,253 A | 6/1982 | Lunn |
| 4,338,313 A | 7/1982 | Teraji et al. |
| 4,339,449 A | 7/1982 | Hashimoto et al. |
| 4,363,807 A | 12/1982 | Takaya et al. |
| 4,367,228 A | 1/1983 | Takaya et al. |
| 4,368,325 A | 1/1983 | Ueda et al. |
| 4,369,312 A | 1/1983 | Hashimoto et al. |
| 4,370,326 A | 1/1983 | Takaya et al. |
| 4,381,299 A | 4/1983 | Teraji et al. |
| 4,390,534 A | 6/1983 | Teraji et al. |
| 4,394,384 A | 7/1983 | Takaya et al. |
| 4,402,955 A | 9/1983 | Lunn |
| 4,405,617 A | 9/1983 | Takaya et al. |
| 4,407,798 A | 10/1983 | Kamiya et al. |
| 4,409,214 A | 10/1983 | Takaya et al. |
| 4,409,215 A | 10/1983 | Takaya et al. |
| 4,409,217 A | 10/1983 | Takaya et al. |
| 4,416,879 A | 11/1983 | Takaya et al. |
| 4,420,477 A | 12/1983 | Takaya et al. |
| 4,423,213 A | 12/1983 | Takaya et al. |
| 4,425,340 A | 1/1984 | Teraji et al. |
| 4,425,341 A | 1/1984 | Takaya et al. |
| 4,427,677 A | 1/1984 | Takaya et al. |
| 4,430,499 A | 2/1984 | Wheeler |
| 4,431,642 A | 2/1984 | Teraji et al. |
| 4,436,912 A | 3/1984 | Wheeler |
| 4,438,113 A | 3/1984 | Takaya et al. |
| 4,443,443 A | 4/1984 | Ueda et al. |
| 4,443,444 A | 4/1984 | Takaya et al. |
| 4,447,429 A | 5/1984 | Teraji et al. |
| 4,450,270 A | 5/1984 | Lunn |
| 4,452,851 A | 6/1984 | Takaya et al. |
| 4,457,928 A | 7/1984 | Teraji et al. |
| 4,462,999 A | 7/1984 | Takaya et al. |
| 4,463,000 A | 7/1984 | Teraji et al. |
| 4,463,002 A | 7/1984 | Takaya et al. |
| 4,463,003 A | 7/1984 | Takaya et al. |
| 4,464,369 A | 8/1984 | Takaya et al. |
| 4,470,980 A | 9/1984 | Higuchi et al. |
| 4,474,779 A | 10/1984 | Nagano et al. |
| 4,477,447 A | 10/1984 | Ueda et al. |
| 4,487,768 A | 12/1984 | Takaya et al. |

(Continued)

FOREIGN PATENT DOCUMENTS

| | | |
|---|---|---|
| AU | 614793 B1 | 5/1989 |
| AU | 707730 B2 | 5/1996 |

(Continued)

OTHER PUBLICATIONS

Yotsuji et al. (Antimicrobial Agents and Chemotherapy, Dec. 1988, p. 1848-1853).*

Bulik et al, In vivo comparison of CXA-101 with and without tazobactam versus piperacillin-tazobactam using human simulated exposures against phenotypically diverse gram-negative organisms. Antimicrob Agent Chemother 2012 56 (1):544-9.

Clinical and Laboratory Standards Institute CLSI Document M07-A9, 2012.

(Continued)

*Primary Examiner* — Jeffrey S. Lundgren
*Assistant Examiner* — William Lee
(74) *Attorney, Agent, or Firm* — Lathrop & Gage LLP; Brian C. Trinque

(57) ABSTRACT

The cephalosporin compound of formula (I) is disclosed, which exhibits antibiotic activity against Gram-negative (e.g., *Pseudomonas aeruginosa*) and Gram-positive (e.g., methicillin-resistant *Staphylococcus aureus*) bacteria. Methods of manufacturing the compound of formula (I), and uses of the compound in the preparation of pharmaceutical compositions and antibacterial applications are also disclosed.

7 Claims, 6 Drawing Sheets

(56) References Cited

U.S. PATENT DOCUMENTS

| | | | |
|---|---|---|---|
| 4,495,182 A | 1/1985 | Teraji et al. |
| 4,496,562 A | 1/1985 | Takaya et al. |
| 4,499,088 A | 2/1985 | Takaya et al. |
| 4,501,739 A | 2/1985 | Lunn et al. |
| 4,515,788 A | 5/1985 | Takaya et al. |
| 4,521,413 A | 6/1985 | Teraji et al. |
| 4,546,101 A | 10/1985 | Takaya et al. |
| 4,550,102 A | 10/1985 | Teraji et al. |
| 4,559,334 A | 12/1985 | Takaya et al. |
| 4,563,449 A | 1/1986 | Teraji et al. |
| 4,577,014 A | 3/1986 | Lunn et al. |
| 4,584,290 A | 4/1986 | Takaya et al. |
| 4,585,872 A | 4/1986 | Teraji et al. |
| 4,590,186 A | 5/1986 | Takaya et al. |
| 4,600,772 A | 7/1986 | O'Callaghan et al. |
| 4,608,373 A | 8/1986 | Shibanuma et al. |
| 4,609,730 A | 9/1986 | Takaya et al. |
| 4,622,318 A | 11/1986 | Takaya et al. |
| 4,626,384 A | 12/1986 | Tanaka et al. |
| 4,631,274 A | 12/1986 | Takaya et al. |
| 4,640,915 A | 2/1987 | Hashimoto et al. |
| 4,647,556 A | 3/1987 | Lattrell et al. |
| 4,667,028 A | 5/1987 | Schwab et al. |
| 4,690,921 A | 9/1987 | Shibanuma et al. |
| 4,692,443 A | 9/1987 | Katner |
| 4,698,337 A | 10/1987 | Takaya et al. |
| 4,699,980 A | 10/1987 | Shibanuma et al. |
| 4,703,046 A | 10/1987 | Ueda et al. |
| 4,705,851 A | 11/1987 | Takaya et al. |
| 4,735,937 A | 4/1988 | Heusler et al. |
| 4,748,172 A | 5/1988 | Katner |
| 4,761,410 A | 8/1988 | Takaya et al. |
| 4,764,606 A | 8/1988 | Imai et al. |
| 4,808,711 A | 2/1989 | Shimizu et al. |
| 4,822,787 A | 4/1989 | Murata et al. |
| 4,833,134 A | 5/1989 | Kishimoto et al. |
| 4,861,769 A | 8/1989 | Takaya et al. |
| 4,868,174 A | 9/1989 | Takaya et al. |
| 4,871,730 A | 10/1989 | Takaya et al. |
| 4,882,434 A | 11/1989 | Yoshioka |
| 4,921,852 A | 5/1990 | Murata et al. |
| 4,923,857 A | 5/1990 | Murata et al. |
| 4,927,818 A | 5/1990 | Takaya et al. |
| 4,935,507 A | 6/1990 | Takaya et al. |
| 4,943,567 A | 7/1990 | Nishizawa et al. |
| 4,952,578 A | 8/1990 | Sakane et al. |
| 4,960,766 A | 10/1990 | Takaya et al. |
| 4,963,543 A | 10/1990 | Murata et al. |
| 4,963,544 A | 10/1990 | Murata et al. |
| 4,971,962 A | 11/1990 | Oh et al. |
| 4,982,596 A | 1/1991 | Peterson et al. |
| 5,036,064 A | 7/1991 | Gotschi |
| RE33,778 E | 12/1991 | Iwanami et al. |
| 5,071,979 A | 12/1991 | Lattrell et al. |
| 5,073,550 A | 12/1991 | Gotschi |
| 5,081,116 A | 1/1992 | Nagano et al. |
| 5,095,012 A | 3/1992 | Okita et al. |
| 5,102,877 A | 4/1992 | Murata et al. |
| 5,104,866 A | 4/1992 | Sakane et al. |
| 5,108,997 A | 4/1992 | Takaya et al. |
| 5,109,130 A | 4/1992 | Sakane et al. |
| 5,138,066 A | 8/1992 | Gotschi |
| 5,159,070 A | 10/1992 | Heymes et al. |
| 5,162,520 A | 11/1992 | Takaya et al. |
| 5,173,485 A | 12/1992 | Sakane et al. |
| 5,179,485 A | 1/1993 | Tamayama |
| 5,187,160 A | 2/1993 | Sakane et al. |
| 5,210,080 A | 5/1993 | Takaya et al. |
| 5,215,982 A | 6/1993 | Sakane et al. |
| 5,215,983 A | 6/1993 | Murata et al. |
| 5,219,848 A | 6/1993 | Hennequin et al. |
| 5,234,920 A | 8/1993 | Okita et al. |
| 5,244,890 A | 9/1993 | Yamanaka et al. |
| 5,281,589 A | 1/1994 | Kim et al. |
| 5,286,721 A | 2/1994 | Murata et al. |
| 5,319,140 A | 6/1994 | Gotschi |
| 5,329,002 A | 7/1994 | Albrecht et al. |
| 5,336,768 A | 8/1994 | Albrecht et al. |
| 5,366,970 A | 11/1994 | Sakane et al. |
| 5,389,627 A | 2/1995 | Kim et al. |
| 5,498,787 A | 3/1996 | Wang et al. |
| 5,523,400 A | 6/1996 | Wei et al. |
| 5,593,985 A | 1/1997 | Kim et al. |
| 5,637,580 A | 6/1997 | White et al. |
| 5,646,139 A | 7/1997 | White et al. |
| 5,648,346 A | 7/1997 | White et al. |
| 5,656,623 A | 8/1997 | White et al. |
| 5,661,144 A | 8/1997 | Tsushima et al. |
| 5,663,163 A | 9/1997 | Takaya et al. |
| 5,763,603 A | 6/1998 | Trickes |
| 6,214,818 B1 | 4/2001 | Nishitani et al. |
| 6,458,950 B1 | 10/2002 | Nishitani et al. |
| 6,518,263 B1 | 2/2003 | Nishitani et al. |
| 6,800,621 B2 | 10/2004 | Nishitani et al. |
| 6,878,686 B2 | 4/2005 | Marquess et al. |
| 6,974,797 B2 | 12/2005 | Fatheree et al. |
| 6,995,138 B2 | 2/2006 | Marquess et al. |
| 7,067,481 B2 | 6/2006 | Fatheree et al. |
| 7,067,482 B2 | 6/2006 | Fatheree et al. |
| 7,129,232 B2 | 10/2006 | Ohki et al. |
| 7,179,801 B2 | 2/2007 | Ohki et al. |
| 7,192,943 B2 | 3/2007 | Yamanaka et al. |
| 7,279,458 B2 | 10/2007 | Fatheree et al. |
| 7,332,471 B2 | 2/2008 | Fatheree et al. |
| 7,341,993 B2 | 3/2008 | Fatheree et al. |
| 7,384,928 B2 | 6/2008 | Nishitani et al. |
| 7,417,143 B2 | 8/2008 | Gnanaprakasam et al. |
| 7,553,962 B2 | 6/2009 | Fatheree et al. |
| 7,601,690 B2 | 10/2009 | Fatheree et al. |
| 7,612,037 B2 | 11/2009 | Fatheree et al. |
| 7,649,080 B2 | 1/2010 | Fatheree et al. |
| 7,655,621 B2 | 2/2010 | Fatheree et al. |
| 7,728,127 B2 | 6/2010 | Fatheree et al. |
| 8,476,245 B2 | 7/2013 | Pourmotabbed et al. |
| 2002/0115650 A1 | 8/2002 | Glinka |
| 2003/0130173 A1 | 7/2003 | Fatheree et al. |
| 2006/0241017 A1 | 10/2006 | Chandran |
| 2006/0287244 A1 | 12/2006 | Chandran |
| 2007/0191280 A1 | 8/2007 | Kelleher |
| 2007/0219191 A1 | 9/2007 | Nishitani et al. |
| 2008/0103299 A1 | 5/2008 | Fatheree et al. |
| 2009/0137460 A1 | 5/2009 | Marquess et al. |
| 2011/0136763 A1 | 6/2011 | Xia et al. |
| 2011/0207658 A1 | 8/2011 | Kelleher |
| 2013/0065874 A1 | 3/2013 | Chandorkar et al. |

FOREIGN PATENT DOCUMENTS

| | | |
|---|---|---|
| AU | 2002952355 | 10/2002 |
| AU | 2003904813 | 9/2003 |
| AU | 2003905084 | 9/2003 |
| CA | 1235689 A1 | 4/1988 |
| CA | 2140701 A1 | 7/1995 |
| CN | 99100092.7 | 12/1999 |
| CN | 200810238479.7 | 5/2009 |
| CN | 200910169647.6 | 4/2010 |
| CN | 201010557481.8 | 4/2011 |
| CN | 201110061045.6 | 3/2012 |
| EP | 0047977 B1 | 9/1981 |
| EP | 0111934 A2 | 6/1984 |
| EP | 0111934 B1 | 8/1984 |
| EP | 137440 A2 | 4/1985 |
| EP | 0137442 A2 | 4/1985 |
| EP | 0137442 A3 | 4/1985 |
| EP | 84111744 | 4/1985 |
| EP | 84306866 | 4/1985 |
| EP | 0318767 A2 | 6/1989 |
| EP | 318767 A2 | 6/1989 |
| EP | 0664117 A1 | 7/1995 |
| EP | 0678095 | 10/1995 |
| EP | 0711774 A1 | 5/1996 |
| EP | 711774 A1 | 5/1996 |
| EP | 1134222 B1 | 4/2005 |
| EP | 1554287 | 7/2005 |

(56) References Cited

FOREIGN PATENT DOCUMENTS

| | | |
|---|---|---|
| EP | 1587497 | 10/2005 |
| EP | 1711178 | 10/2006 |
| EP | 1799209 | 6/2007 |
| EP | 1919449 | 5/2008 |
| EP | 2015755 | 1/2009 |
| EP | 2063869 | 6/2009 |
| EP | 2086570 | 8/2009 |
| EP | 2120880 | 11/2009 |
| EP | 2136844 | 12/2009 |
| EP | 2203177 | 7/2010 |
| EP | 2280713 | 9/2011 |
| EP | 1154770 | 11/2011 |
| EP | 2440523 | 4/2012 |
| JP | 62103092 A | 5/1987 |
| JP | 62158290 A | 7/1987 |
| JP | 63051388 A | 3/1988 |
| JP | 63051389 A | 3/1988 |
| JP | 02088582 | 3/1990 |
| JP | 2088582 A | 3/1990 |
| JP | 02117678 | 5/1990 |
| JP | 2117678 A | 5/1990 |
| JP | 4288086 A | 10/1992 |
| JP | 05222058 | 8/1993 |
| JP | 5222058 A | 8/1993 |
| JP | 06056848 | 3/1994 |
| JP | 6056848 A | 3/1994 |
| JP | 6128268 A | 5/1994 |
| JP | 3140525 | 12/2000 |
| JP | 3141040 | 12/2000 |
| JP | 3141041 | 12/2000 |
| JP | 3145483 | 1/2001 |
| JP | 2005162670 A | 6/2005 |
| WO | WO 99/28308 | 6/1999 |
| WO | WO 99/64049 | 12/1999 |
| WO | WO0004915 A1 | 2/2000 |
| WO | WO 2004/048551 | 6/2004 |
| WO | WO 2005/005436 | 1/2005 |
| WO | WO 2005/005436 A3 | 1/2005 |
| WO | WO 2007/099396 A3 | 9/2007 |
| WO | WO 2009/049086 | 4/2009 |
| WO | WO 2009/105782 | 8/2009 |
| WO | WO2013036783 A2 | 3/2013 |

OTHER PUBLICATIONS

Clinical and Laboratory Standards Institute CLSI Document M100-S22, 2012.
Melchers et al., In vitro Activity of CXA-101 Alone and in Combination With Tazobactam Against Extended Spectrum Beta-lactamase Harbouring Enterobacteriaceae. 52nd Annual Interscience Conference on Antimicrobial Agents and Chemotherapy (ICAAC 2012); Sep. 9-12, 2012. Poster F1-2008.
GE et al., Pharmacokinetics and safety of CXA-101, a new antipseudomonal cephalosporin, in healthy adult male and female subjects receiving single- and multiple-dose intravenous infusions. Antimicrob Agents Chemother. 2010 ; 54: 3427-31.
Juan et al., Activity of a new antipseudomonal cephalosporin, CXA-101, against carbapenem-resistant and multidrug-resistant *Pseudomonas aeruginosa* clinical strains. Antimicrob Agents Chemother. 2010:54(2):846-51.
Sader et al., Antimicrobial activity of CXA-101, a novel cephalosporin tested in combination with tazobactam against Enterobacteriaceae, *Pseudomonas aeruginosa*, and Bacteroides fragilis strains having various resistance phenotypes. Antimicrob Agents Chemother. 2011 55(5):2390-4.
Cabot et al. Dynamics and mechanisms of resistance development to ceftazidime, meropenem and ceftolozane-/tazobactam in wild-type and mutator *P. aeruginosa* strains. 52nd Annual Interscience Conference on Antimicrobial Agents and Chemotherapy (ICAAC 2012); Sep. 9-12, 2012. Poster C1-1970.
Reynolds et al., Enterobacteriaceae in the UK and Ireland: Susceptibility to Old and New Agents. 52nd Annual Interscience Conference on Antimicrobial Agents and Chemotherapy (ICAAC 2012); Sep. 9-12, 2012. Poster C2-152.

Moya et al., Pan-β-Lactam Resistance Development in *Pseudomonas aeruginosa* Clinical Strains: Molecular Mechanisms, Penicillin-Binding Protein Profiles, and Binding Affinities. Antimicrob Agents Chemother. 2012 56 4771-8.
Chandorkar et al., Intrapulmonary penetration of ceftolozane/tazobactam and piperacillin/tazobactam in healthy adult subjects. J Antimicrob Chemother. 2012, 67, 2463.
Miller et al., Pharmacokinetics and Safety of Intravenous Ceftolozane/tazobactam in Healthy Adult Subjects following Single and Multiple Ascending Doses. Antimicrob Agents Chemother. 2012 56:3086-91.
Moya et al., Affinity of the New Cephalosporin CXA-101 to Penicillin-Binding Proteins of *Pseudomonas aeruginosa*. Antimicrob Agents Chemother. 2010; 54: 3933-3937.
Livermore et al., Chequerboard titration of cephalosporin CXA-101 and tazobactam versus beta-lactamase-producing Enterobacteriaceae. J Antimicrob Chemother. 2010 65 1972-4.
Zamorano et al., Activity of the new cephalosporin CXA-101 against *Pseudomonas aeruginosa* isolates from chronically-infected cystic fibrosis patients. Clin Microbiol Infect. 2010 16(9):1482-7.
Riera et al., Anti-biofilm and resistance suppression activities of CXA-101 against chronic respiratory infection phenotypes of *Pseudomonas aeruginosa* strain PAO1. J Antimicrob Chemother. 2010;65(7):1399-404.
Moya et al., Activity of a new cephalosporin, CXA-101 (FR264205), against beta-lactam-resistant *Pseudomonas aeruginosa* mutants selected in vitro and after antipseudomonal treatment of intensive care unit patients. Antimicrob Agents Chemother. 2010 ;54(3):1213-7.
Bulik et al., In vitro potency of CXA-101, a novel cephalosporin, against *Pseudomonas aeruginosa* displaying various resistance phenotypes, including multidrug resistance. Antimicrob Agents Chemother. 2010;54(1):557-9.
Perletti et al., CXA-10—Cephalosporin Antibiotic. Drugs of the Future 2010; 35(12): 977-986.
Livermore et al., Activity of cephalosporin CXA-101 against *Pseudomonas aeruginosa* and *Burkholderia cepacia* group strains and isolates. Int J Antimicrob Agents. 2009 ;34(5):402-6.
Giske et al., Activity of cephalosporin CXA-101 and comparators against extended-spectrum-{beta}-lactamase-producing *Pseudomonas aeruginosa*. J Antimicrob Chemother. 2009 ;64(2):430-1.
Toda et al., Synthesis and SAR of novel parenteral anti-pseudomonal cephalosporins: discovery of FR264205. Bioorg Med Chem Lett. 2008 ;18(17):4849-52.
Takeda et al., Stability of FR264205 against AmpC beta-lactamase of *Pseudomonas aeruginosa*. Int J Antimicrob Agents. Nov. 2007;30(5):443-5.
Bulik et al., In vitro activity of CXA-101, a novel cephalosporin, against resistant phenotypes of *Pseudomonas aeruginosa*. 47th Annual Meeting of the Infectious Diseases Society (IDSA 2009); Oct. 29-Nov. 1, 2009. Poster 209.
Livermore et al. Chequerboard titrations of cephalosporin CXA-101 and tazobactam vs. beta-lactamase producing Enterobacteriaceae. 49th Annual Interscience Conference on Antimicrobial Agents and Chemotherapy (ICAAC 2009); Sep. 12-15, 2009. Poster F1-1994.
Moya et al. Activity of CXA-101 against *Pseudomonas aeruginosa* beta-lactam resistance mechanisms: ampD, ampDh2, ampDh2, dacB, and oprD mutations. 49th Annual Interscience Conference on Antimicrobial Agents and Chemotherapy (ICAAC 2009); Sep. 12-15, 2009. Poster F1-1989.
Soon et al. A Novel Mathematical Modeling Approach to Characterize the Pharmacodynamics of Ceftolozane/Tazobactam, a β-lactam & β-lactamase Inhibitor Combination. 52nd Annual Interscience Conference on Antimicrobial Agents and Chemotherapy (ICAAC 2012); Sep. 9-12, 2012. Oral Presentation A*1762.
Miller et al. CXA-201 dose selection based on probability of target attainment and drug exposure in subjects with varying degrees of renal impairment. ICAAC 2011. Oral Presentation A-1099.
Steenbergen et al. Potency of CXA-101Tazobactam for Pathogens from ICU and non-ICU Correlated to Probability of Pharmacokinetic/Pharmacodynamic (PK/PD) Target Attainment. ICAAC 2011. Oral Presentation A-1689.

(56) References Cited

OTHER PUBLICATIONS

Hatano et al. In vivo Anti-*Pseudomonas Aeruginosa* Activity of Novel Parenteral Cephalosporin, FR264205. 45th Annual Interscience Conference on Antimicrobial Agents and Chemotherapy (ICAAC 2005); Dec. 16-19, 2005. Oral Presentation F-1165.

Strayer et al. Pharmacodynamics of Piperacillin Alone and in Combination with Tazobactam against Piperacillin-Resistant and -Susceptible Organisms in an In Vitro Model of Infection. Antimicrobial Agents and Chemotherapy 1994;38:2351.

Bush et al. Kinetic Interactions of Tazobactam with Beta-Lactamases from All Major Structural Classes. Antimicrobial Agents and Chemotherapy 1993;37:851.

Kurpiel. Point Mutations in the Inc Antisense RNA Gene Are Associated with Increased Plasmid Copy Number, Expression of BIaCMY-2 and Resistance to Piperacillin/Tazobactam in *Escherichia coli*. Journal of Antimicrobial Chemotherapy 2012;67:339.

Lister et al. Importance of Beta-Lactamase Inhibitor Pharmacokinetics in the Pharmacodynamics of Inhibitor-Drug Combinations: Studies with Piperacillin-Tazobactam and Piperacillin-sulbactam. Antimicrobial Agents and Chemotherapy 1997;41:721.

Thomson et al. Beta-Lactamase Production in Memebers of the Family Enterobacteriaceae and Resistance to Beta-Lactam-Enzyme Inhibitor Combinations. Antimicrobial Agents and Chemotherapy 1990;34:622.

Seetulsingh et al. Activity of Clavulanate Combinations against TEM-1 b-Lactamase-Producing *Escherichia coli* Isolates Obtained in 1982 and 1989. Journal of Antimicrobial Chemotherapy 1991;27:749.

Alexov et al. Efficacy of Ampicillin-Sulbactam Is not Dependent upon Maintenance of a Critical Ratio between Components: Sulbactam Pharmacokinetics in Pharmacodynamic Interactions. Antimcirobial Agents Chemotherapy 1996;40:2468.

Louie et al., Pharmacodynamics of b-Lactamase Inhibition by NXL104 in Combination with Cefaroline: Examining Organisms with Multiple Types of b-Lacramases. Antimicrobial Agents and Chemotherapy. 2012, 56, 258.

Abstract for Moulds et al.,. Impact of characterized resistance mechanisms on the susceptibility of *Pseudomonas aeruginosa* to CXA-101. 50th Annual Interscience Conference on Antimicrobial Agents and Chemotherapy (ICAAC 2010); Sep. 12-15, 2010. Poster C1-1415; This poster is obtainable at: http://www.cubist.com/downloads/Moulds.PP.ICAAC_2010.Impact_of_resis_mech_on_suscep_of_P_aeruginosa_to_CXA_JNS.pdf.

Abstract for Umeh et al., A double-blind, randomized, phase 2 study to compare the safety and efficacy of intravenous CXA-101 and intravenous ceftazidime in complicatged urinary tract infection. 50th Annual Interscience Conference on Antimicrobial Agents and Chemotherapy (ICAAC 2010); Sep. 12-15, 2010. Poster L1-361A; This poster is obtainable at: http://www.cubist.com/downloads/Umeh_ICAAC2010_08144v2.pdf.

Abstract for Brown et al. Activity profile of CXA-101 and CXA-101/tazobaciam against target gram-positive and gram-negative pathogens. 49th Annual Interscience Conference on Antimicrobial Agents and Chemotherapy (ICAAC 2009); Sep. 12-15, 2009. Poster F1-1986; This poster is obtainable at : http://www.eurofins.com/media/767069/Final%20F1-1986.pdf.

Abstract for Brown et al., Disk diffusion testing of CXA-101 and CXA-101 in combination with tazobactam against target pathogens. 49th Annual interscience Conference on Antimicrobial Agents and Chemotherapy (ICAAC 2009); Sep. 12-15, 2009. Poster F1-1998; this poster is obtainable at: http://www.eurofins.com/media/767072/Final%20F1-1998.pdf.

Abstract for Brown et al., Quality control parameters for CXA-101 broth microdilution susceptibility tests. 49th Annual Interscience Conference on Antimicrobial Agents and Chemotherapy (ICAAC 2009); Sep. 12-15, 2009. Poster F1-1997.

Abstract for Craig et al., In vivo activity of CXA-101 plus a 2:1, 4:1, or 8:1 ratio of tazobactam against various Enterobacteriaceae producing Extended-spectrum beta-lactamases in the thighs of neutropenic mice. 49th Annual Interscience Conference on Antimicrobial Agents and Chemotherapy (ICAAC 2009); Sep. 12-15, 2009. Poster F1-1999.

Abstract for Craig et al., In vivo activity of CXA-101, a new cephalosporin, against *Pseudomonas aeruginosa* and other Enterobacteriaceae in the thighs of neutropenic mice. 49th Annual Interscience Conference on Antimicrobial Agents and Chemotherapy (ICAAC 2009); Sep. 12-15, 2009. Poster F1-2002.

Abstract for Ge et al., CXA-101 population PK analysis and Monte Carlo simulation for PK/PD target attainment and dose regimen selection. 49th Annual Interscience Conference on Antimicrobial Agents and Chemotherapy (ICAAC 2009); Sep. 12-15, 2009. Poster F1-2003.

Abstract for Ge et al., PK study of CXA-101 in combination with tazobactam in dogs after intravenous administration. 49th Annual Interscience Conference on Antimicrobial Agents and Chemotherapy (ICAAC 2009); Sep. 12-15, 2009. Poster F1-2001.

Abstract for Ge et al., PK and safety of CXA-101, a new antipseudomonal cephalosporin, in healthy adult subjects after single intravenous dosing. 49th Annual Interscience Conference on Antimicrobial Agents and Chemotherapy (ICAAC 2009); Sep. 12-15, 2009. Poster F1-2004.

Abstract for Giske et al., CXA-101 has high activity against clinical isolates of *Pseudomonas aeruginosa* including ceftazidime-resistant isolates. 49th Annual lnterscience Conference on Antimicrobial Agents and Chemotherapy (ICAAC 2009); Sep. 12-15, 2009. Poster F1-1988.

Abstract for Jacqueline et al. FIC Index determination of CXA-101/tazobactam in combination with amikacin, aztreonam, meropenem, levofloxacin, and tigecycline against *Escherichia coli, Klebsiella pneumoniae*, and *Pseudomonas aeruginosa* strains. 49th Annual Interscience Conference on Antimicrobial Agents and Chemotherapy (ICAAC 2009); Sep. 12-15, 2009. Poster F1-1995.

Abstract for Jacqueline et al. In vitro assessment using time-kill curves of CXA-101/tazobactam against *Escherichia coli, Klebsiella pneumoniae*, and *Pseudomonas aeruginosa* strains. 49th Annual Interscience Conference on Antimicrobial Agents and Chemotherapy (ICAAC 2009); Sep. 12-15, 2009. Poster F1-1996.

Abstract for Jacqueline et al. 50% effective dose determination of CXA-101 alone or in combination with tazobactam for treating experimental peritonitis in mice due to extended-spectrum beta-lactamase-producing *Escherichia coli* strains: comparison with ceftazidime and piperacillin/tazobactam. 49th Annual Interscience Conference on Antimicrobial Agents and Chemotherapy (ICAAC 2009); Sep. 12-15, 2009. Poster F1-2000.

Abstract for Juan et al., Oliver A. Activity of the new cephalosporin CXA-101 against carbapenem-resistant *Pseudomonas aeruginosa* isolates from a Spanish multicenter study. 49th Annual Interscience Conference on Antimicrobial Agents and Chemotherapy (ICAAC 2009); Sep. 12-15, 2009. Poster F1-1987.

Abstract for Moya et al. Affinity of the new cephalosporin CXA-101 to penicillin-binding proteins of *Pseudomonas aeruginosa*. 49th Annual Interscience Conference on Antimicrobial Agents and Chemotherapy (ICAAC 2009); Sep. 12-15, 2009. Poster F1-1985.

Abstract for Riera et al. Activity of the new cephalosporin CXA-101 against biofilms of relevant *P. aeruginosa* phenotypes in cystic fibrosis chronic respiratory infection: mucoid and hypermutable strains. 49th Annual Interscience Conference on Antimicrobial Agents and Chemotherapy (ICAAC 2009); Sep. 12-15, 2009. Poster F1-1990.

Abstract for Sader et al., Activity of the novel cephalosporin CXA-101 tested in combination with tazobactam against cephalosporin-resistant Enterobacteriaceae, *P. aeruginosa* and *B. fragilis*. 49th Annual Interscience Conference on Antimicrobial Agents and Chemotherapy (ICAAC 2009); Sep. 12-15, 2009. Poster F1-1992; This poster is obtainable at: http://www.jmilabs.com/data/posters/ICAAC2009/F1-1992.pdf.

Abstract for Titelman et al. Activity of CXA-101 plus tazobactam against ESBL-producing *E. coli* and *K. pneumoniae* 49th Annual Interscience Conference on Antimicrobial Agents and Chemotherapy (ICAAC 2009); Sep. 12-15, 2009. Poster F1-1993.

Abstract for Zamorano et al. Activity of the new cephalosporin CXA-101 against *P. aeruginosa* isolates from chronically infected cystic

(56) References Cited

OTHER PUBLICATIONS fibrosis patients. 49th Annual Interscience Conference on Antimicrobial Agents and Chemotherapy (ICAAC 2009); Sep. 12-15, 2009. Poster F1-1991.

Abstract for Brown et al. Activity profile of CXA-101 against gram-positive and gram-negative pathogens by broth and agar dilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-354; This poster is obtainable at: http://www.eurofins.com/media/694466/Calixa%20F1-354%20broth%20agar%20v6.pdf.

Abstract for Brown et al. Effect of various testing parameters on the activity of CXA-101 by broth microdilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-357; This poster is obtainable at: http://www.eurofins.com/media/694469/CXA%20F1-357%20parameter%20v6.pdf.

Abstract for Brown et al. Mode of action of CXA-101 based on minimum bactericidal concentration analysis and time-kill kinetic analysis. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-358; This poster is obtainable at: http://www.eurofins.com/media/694472/CXA%20F1-358%20tk%20mbc%20v5.pdf.

Abstract for Livermore et al., Warner M. Activity of cephalosporin CXA-101 vs. *P. aeruginosa*. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-355; This poster is obtainable at: http://www.hpa.org.uk/webc/HPAwebFile/HPAweb_C/1225354148015.

Abstract for Mushtaq et al. Activity of cephalosporin CXA-101 with B-lactamase inhibitors vs. Enterobacteriaceae. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-356; This poster is obtainable at: http://www.hpa.org.uk/webc/HPAwebFile/HPAweb_C/1225354148047.

Abstract for Sader et al., Activity of the Novel Antimicrobial Ceftolozane/Tazobactam Tested Against Bacterial Isolates in USA Hospitals from Patients with Pneumonia (2011). IDWeek 2012: A Joint Meeting of IDSA, SHEA, HIVMA, and PIDS; Oct. 17-21, 2012. Poster 846; This poster is obtainable at: http://www.jmilabs.com/data/posters/IDWeek2012/846.pdf.

Abstract for Walkty et al. In Vitro Activity of Ceftolozane/Tazobactam (CXA-201) versus *Pseudomonas aeruginosa* Isolates Obtained from Patients in Canadian Hospitals: CANWARD 2011. IDWeek 2012: A Joint Meeting of IDSA, SHEA, HIVMA, and PIDS; Oct. 17-21, 2012. Poster 1616; This poster is obtainable at: https://idsa.confex.com/idsa/2012/webprogram/Handout/id509/POSTER202_1616.pdf.

Abstract for Miller et al., Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population. 52nd Annual Interscience Conference on Antimicrobia Agents and Chemotherapy (ICAAC 2012); Sep. 9-12, 2012. Poster A-641.

Abstract for Sader et al., Activity of the Novel Antimicrobial Ceftolozane/Tazobactam Tested Against Contemporary Clinical Strains from USA Hospitals (2011). 52nd Annual Interscience Conference on Antimicrobial Agents and Chemotherapy (ICAAC 2012); Sep. 9-12, 2012. Poster E-199.

Abstract for Soon et al., In vitro Pharmacodynamics of CXA-201 (Ceftolozane/Tazobactam) against β-lactamase Producing *Eschericia coli*. 52nd Annual Interscience Conference on Antimicrobial Agents and Chemotherapy (ICAAC 2012); Sep. 9-12, 2012. Poster E-201.

Abstract for Zhanel et al., In vitro Activity of Ceftolozane/tazobactam Tested Against 1,705 Gram-Negative Pathogens Isolated from Patients in Canadian Hospitals in 2011: CANWARD Surveillance Study. 52nd Annual Interscience Conference on Antimicrobial Agents and Chemotherapy (ICAAC 2012); Sep. 9-12, 2012. Poster E-200.

Abstract for Chandorkar et al. Intrapulmonary penetration of CXA-201 and Piperacillin/tazobactam in healthy adult subjects. 22nd Annual Meeting of the European Congress of Clinical Microbiology (ECCMID 2012); Mar. 31-Apr. 3, 2012. Poster P1627.

Abstract for Sader et al., Activity of the Novel Antimicrobial CXA-201 Tested Against Contemporary Clinical Strains from European Hospitals. 22nd Annual Meeting of the European Congress of Clinical Microbiology (ECCMID 2012); Mar. 31-Apr. 3, 2012. Poster P1446.

Abstract for Snydman et al., Activity of Ceftolozane/Tazobactam CXA-201 against 270 recent isolates from the bacteroides group. 22nd Annual Meeting of the European Congress of Clinical Microbiology (ECCMID 2012); Mar. 31-Apr. 3, 2012. Poster; This poster is obtainable at: http://www.escmid.org/escmid_library/online_lecture_library/?search=1&current_page=1&search_term=snydman.

Abstract for Chandorkar et al. Intrapulmonary penetration of CXA-201 and Piperacillin/tazobactam in healthy adult subjects. 49th Annual Meeting of the Infectious Diseases Society of America (IDSA 2011); Oct. 20-23, 2011. Poster 611.

Abstract for Miller et al. Probability of Target Attainment of CXA-201 in Patients with Renal Hyperclearance. 49th Annual Meeting of the Infectious Diseases Society of America (IDSA 2011); Oct. 20-23, 2011. Poster B1-589.

Abstract for Killian et al. An Equivalency Study of a Sensititre Dried MIC Plate Compared with the CLSI Broth Microdilution Reference Method for CXA-201 and Comparator Antimicrobials. 51st Annual Interscience Conference on Antimicrobial Agents and Chemotherapy (ICAAC 2011); Sep. 17-20, 2011. Poster D-691A.

Abstract for Moya et al. Pan-β-lactam resistance development in *P. aeruginosa* clinical strains: molecular mechanisms, PBPs profiles and binding affinities. 51st Annual Interscience Conference on Antimicrobial Agents and Chemotherapy (ICAAC 2011); Sep. 17-20, 2011. Poster C1-619.

Abstract for Hershberger et al. CXA-101/Tazobactam Probability of Target Attainment Using Population Pharmacokinetic Analysis. Joint Meeting of the European Congress of Clinical Microbiology and Infectious Diseases and International Congress of Chemotherapy (ECCMID-ICC 2011); May 7-12, 2011. Poster 1520; This poster is obtainable at: http://www.poster-submission.com/search/sresult.

Abstract for Miller et al. Pharmacokinetics of CXA-101/tazobactam in Subjects with Mild or Moderate Renal Impairment. Joint Meeting of the European Congress of Clinical Microbiology and Infectious Diseases and International Congress of Chemotherapy (ECCMID-ICC 2011); May 7-12, 2011. Poster 1519; This poster is obtainable at: http://www.poster-submission.com.

Abstract for Fenneteau et al. Population PK/PD Modeling and Simulations of a Fixed-Dose Combination of CXA-101 and Tazobactam to Optimize Dosing Strategies in Renally Impaired Patients with Complicated Urinary Tract Infection. 3rd Biennial American Conference on Pharmacometrics (ACoP 2011); Apr. 3-6, 2011; This poster is obtainable at: http://www.go-acop.org/sites/default/files/webform/posters/ACOP2011%20-%20Dosing%Strategies%20of%20CXA-101%20and%20Taz%20in%20cUTI%20Patients.pdf.

Abstract for Marier et al. Population PK Analysis of Intravenous CXA-101 in Subjects with Complicated Urinary Tract Infection, Including Pyelonephritis. 112th Annual Meeting of the American Society for Clinical Pharmacology and Therapeutics (ASCPT 2011); Mar. 2-5, 2011. Poster PII-49.

Abstract for Bulik et al. In vivo Efficacy of Human Simulated CXA-101 ± Tazobactam versus Piperacillin-Tazobactam against Phenotypically Diverse Gram-negative Organisms. ICAAC 2010. Poster A1-1381; This poster is obtainable at: http://www.cubist.com/downloads/Bulik_PP_ICAAC_2010_in_vivo_CXA-101_vs_TZP_against_gram_neg.pdf.

Abstract for Cabot et al. Activity of CXA-101 Against a Large Collection of *P. aeruginosa* Blood Stream Isolates Overexpressing

(56) References Cited

OTHER PUBLICATIONS

AmpC and the Major Efflux Pumps. 50th Annual Interscience Conference on Antimicrobial Agents and Chemotherapy (ICAAC 2010); Sep. 12-15, 2010. Poster E-816.
Abstract for Jacqueline . Assessment of the In vivo Activity of CXA-101 in a Murine Model of *Pseudomonas aeruginosa* Pneumonia: Comparison with Ceftazidime and Piperacillin-Tazobactam. 50th Annual Interscience Conference on Antimicrobial Agents and Chemotherapy (ICAAC 2010); Sep. 12-15, 2010. Poster B-1401.
Abstract for Marier et al. Pharmacokinetics of a novel anti-pseudomonal cephalosporin, CXA-101, and tazobactam in healthy adult subjects. 50th Annual Interscience Conference on Antimicrobial Agents and Chemotherapy (ICAAC 2010); Sep. 12-15, 2010. Poster A1-1391.
Anderegg et al: Quality Control Guidelines for BAL9141 (Ro 63/9141), an Investigational Cephalosporin, When Reference Mic and Standardized Disk Diffusion Susceptibility Test Methods Are Used; Journal of Clinical Microbiology. (2004), pp. 3356-3358.
Marunaka: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H), in Aqueous Solutions and Alkaline MEthanol Solution: Pathway and Structural Elucidation of Products; Chem. Pharm. Bull.; 1988, vol. 36, pp. 4478-4487.
Matsushima: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H) in Solid State: Structural Eldcidation; Chem. Pharm. Bull.; 1988, vol. 36, pp. 4593-4596.
Murano: Structural requirements for the stability of novel cephalosporins to AmpC beta-lactamase based on 3-D structure; Bioorg. Med. Chem. Lett.; 2007, vol. 16, pp. 2261-2275.
Yoshizawa: New broad-spectrun parenteral cephalosporins exhibiting potent activity against both methicilln-resistant *Staphlococcus aureus* (MRSA) and *Pseudomonas aeruginosa*. Part 3: &Beta-[2-(5-Amino-1,2,4-thiadiazol-3-yl)-2-ethoxtiminoacetamido] cephalosporins bearing 4-[3-(aminoalkyl)-ureido]-1-pyridinium at C3; Bioorg. Med. Chem. Lett.; 2004, vol. 12, pp. 4221-4231.
Wootton et al: BAL 9141, a new borad-spectrum pyrrolidinone cephalosporin: activity against clinically significant anaerobes in comparison with 10 other antimicrobials; Journal of Antimicrobial Chemotherapy; (2002) vol. 49, pp. 535-539.
Search Request Confirmation; Science IP; Dec. 6, 2010, 3 pages.
Ambrose, et al: Pharmacokinetic-pharmacodynamic considerations in the design of hospital-acquired or ventilator-associated bacterial pneumonia studies: look before you leap!; Clin Infect Dis, 2010, vol. 51, Suppl 1, pp. 5103-5110.
American Thoracic Society; Infectious Diseases Society of America; Guidelines for the management of adults with hospital-acquired, ventilator-associated, and healthcare-associated pneumonia; Am J Respir Crit Care Med., 2005, vol. 171(4), pp. 388-416.
Baughman, et al: The diagnosis and treatment challenges in nosocomial pneumonia; Diagn Microbiol Infect Dis, 1999, vol. 33(2), pp. 131-139.
Bergogne-Berezin: Predicting the efficacy of antimicrobial agents in respiratory infections: is tissue concentration a valid measure?; J Antimicrob Chemother, 1995, vol. 35, pp. 363-371.
Boselli, et al: Steady-state plasma and intrapulmonary concentrations of piperacillin/tazobactam 4 g/0.5 g administered to critically ill patients with severe nosocomial pneumonia; Intensive Care Med, 2004, vol. 30, pp. 976-979.
Boselli, et al: Alveolar concentrations of piperacillin/tazobactam administered in continuous infusion to patients with ventilator-associated pneumonia; Crit Care Med, 2008, vol. 36, pp. 1500-1506.
Chastre, et al: Ventilator-associated pneumonia; Am J Respir Crit Care Med, 2002, vol. 165(7), pp. 867-903.
Chastre, et al: Comparison of 8 vs 15 days of antibiotic therapy for ventilator-associated pneumonia in adults: a randomized trial; JAMA, 2003, vol. 290(19), pp. 2588-2598.
El Solh: Update on the treatment of *Pseudomonas aeruginosa* pneumonia; J Antimicrob Chemother, 2009, vol. 64, pp. 229-238.
Zosyn®. Prescribing Information. Wyeth Pharmaceuticals, Inc., Philadelphia, PA, USA; http://labeling.pfizer.com/showlabeling.aspx?id=416 (Apr. 23, 2012, date last accessed), 26 pages.
Harrison's Principles of Internal Medicine: Hospital-Acquired (Nosocomial) Pneumonia; ed. Kasper, et al.; 16th ed. New York: McGraw-Hill, Medical Pub. Division. 2005, pp. 1538-1541.
Jones, et al: Microbial etiologies of hospital-acquired bacterial pneumonia and ventilator-associated bacterial pneumonia; Clin Infect Dis; 2010, Suppl 1, pp. S81-S87.
Joseph, et al: Ventilator-associated pneumonia: A Review; Eur J Intern Med; 2010, vol. 21(5), pp. 360-368.
Klevens, et al: Estimating health care-associated infections and deaths in U.S. hospitals, 2002; Public Health Rep, 2007, vol. 122, pp. 160-166.
Knaus, et al: APACHE II: A severity of disease classification system; Crit Care Med, 1985, vol. 13, pp. 818-829.
Komuro, et al: Inhibition of the renal excretion of tazobactam by piperacillin; J Antimicrob Chemother, 1994, vol. 34, pp. 555-564.
Mesaros, et al. *Pseudomonas aeruginosa*: resistance and therapeutic options at the turn of the new millennium; Clin Microbiol Infect, 2007, vol. 13, pp. 560-578.
Pankey: Tigecycline; J Antimicrob Chemotherapy, 2005, vol. 56, pp. 470-480.
Occhipinti, et al: Pharmacokinetics and pharmacodynamics of two multiple-dose piperacillin-tazobactam regimens; Antimicrob Agents Chemother, 1997, vol. 41, pp. 2511-2517.
Pea: The antimicrobial therapy puzzle: could pharmacokinetic-pharmacodynamic relationships be helpful in addressing the issue of appropriate pneumonia treatment in critically ill patients?; Clin Infect Dis, 2006, vol. 42, pp. 1764-1771.
Richards, et al: Nosocomial infections in medical intensive care units in the United States. National Nosocomial Infections Surveillance System; Crit Care Med, 1999, vol. 27(5), pp. 887-892.
Freire, et al: Comparison of tigecycline with imipenem/cilastatin for the treatment of hospital-acquired penumonia; Diag Microbio and Infec Dis, 2010, vol. 68, pp. 140-151.
Schulgen, et al: Estimation of extra hospital stay attributable to nosocomial infections: heterogeneity and timing of events; J Clin Epidemiol; Apr. 2000, vol. 53(4), pp. 409-417.
Singh:et al: Short-course empiric antibiotic therapy for patients with pulmonary infiltrates in the intensive care unit. A proposed solution for indiscriminate antibiotic prescription; Am J Respir Crit Care Med, Aug. 2000, vol. 162(2, Pt 1), pp. 505-511.
Udy, et al: Augmented renal clearance: implications for antibacterial dosing in the critically ill; Clin Pharmacokinet, 2010, vol. 49(1), pp. 1-16.
Vincent, et al: Use of the SOFA score to assess the incidence of organ dysfunction/failure in intensive care units: results of a multicenter, prospective study. Working group on "sepsis-related problems" of the European Society of Intensive Care Medicine; Crit Care Med, 1998, vol. 26(11), pp. 1793-1800.
Wunderink, et al: Linezolid in methicillin-resistant *Staphylococcus aureus* nosocomial pneumonia: a randomized, controlled study; Clin Infect Dis, 2012, vol. 54(5), pp. 621-629.
Zilberberg, et al: Epidemiology of healthcare-associated pneumonia (HCAP); Semin Respir Crit Care Med, 2009, vol. 30, pp. 10-15.
Lucasti: A Phase 3, Randomized, Double-Blind Study of Ceftobiprole Medocaril Versus Linezolid Plus Ceftazidime in the Treatment of Nosocomial Pneumonia; Ceftobiprole: Clinical Study Report Synopsis BAP00248/307; Issue Date: Jul. 14, 2010; Document No. EDMS-PSDB-6906024:3.0, (8 pages).

* cited by examiner

CEPHALOSPORIN COMPOUND

RELATED APPLICATIONS

The present application claims priority to U.S. Provisional Application No. 61/698,241, filed on Sep. 7, 2012, which is incorporated herein by reference in its entirety.

TECHNICAL FIELD

This disclosure is directed to a cephalosporin compound which is useful as an antibiotic, as well as pharmaceutical compositions comprising the compound, methods of using the compound as an antibacterial agent, and processes and intermediates for preparing the compound.

BACKGROUND

A variety of cephalosporin derivative compounds with various substitutions on a beta-lactam core have antibacterial activity. Cephalosporin compounds with a quaternary ammonium group at the 3-position of the cephalosporin beta lactam core structure and an aminothiazole/oxime structure at the 7-position can provide antibacterial activity against multiple types of bacteria, including Gram-negative bacteria *Pseudomonas aeruginosa* (Pa). For example, ceftazidime and cefpirome, which include the cephalosporin core with an aminothiazolyl group at the 7-position and a quaternary salt substituent at the 3-position, have antibacterial activity against a wide spectrum of bacteria from Gram-positive bacteria in addition to *Pseudomonas aeruginosa*. However, even compounds such as ceftazidime and cefpirome may not be satisfactory in the antibacterial activity against both *Pseudomonas aeruginosa* and methicillin-resistant *Staphylococcus aureus* (MRSA). In addition, infectious diseases caused by methicillin-resistant *Staphylococcus aureus* (MRSA) continue to present significant clinical challenges. There remains a need for novel cephalosporin antibiotics which have improved antibacterial activity also against these and other bacteria.

SUMMARY

A cephalosporin compound with antibacterial activity against Gram-negative and Gram-positive bacteria, including *Pseudomonas aeruginosa* and methicillin-resistant *Staphylococcus aureus* (MRSA), is disclosed. In particular, this disclosure provides a cephalosporin compound of formula (I) having antibacterial activity against both *Pseudomonas aeruginosa* and methicillin-resistant *Staphylococcus aureus* (MRSA), for example as measured according to Minimum Inhibitory Concentrations (MICs) as measured by the method of Examples 3-5.

Provided herein is a cephalosporin compound having the structure:

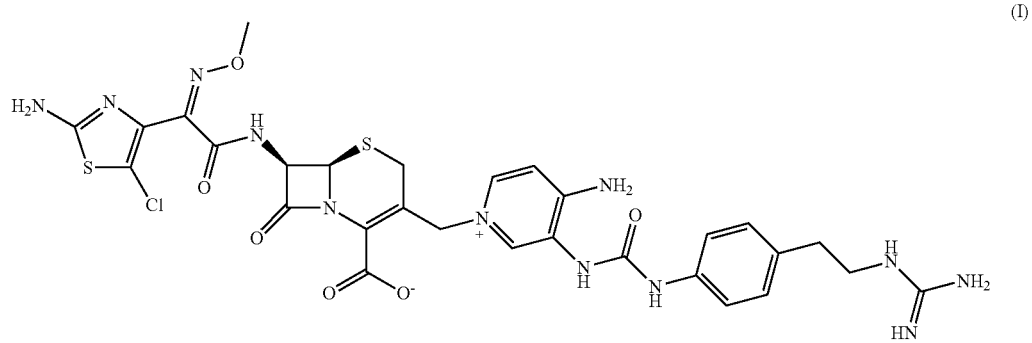

(I)

The cephalosporin compound of formula (I) has antibacterial activity against both Gram-negative bacteria and Gram-positive bacteria and is useful in treating a bacterial infection in a host, such as a human or other mammal. For example, pharmaceutical compositions comprising formula (I), or a pharmacologically acceptable salts thereof, can be independently effective against both Gram-negative bacteria such as *Pseudomonas aeruginosa* and Gram-positive bacteria such as *Staphylococcus aureus*—including MRSA—with a MIC of not more than about 4 micrograms/mL (as measured according to the method of Example 3). Methods of treating bacterial infections can include administering to an infected host a pharmaceutical composition comprising an antibacterially effective amount of the compound of formula (I), or a pharmacologically acceptable salt thereof.

The compound of formula (I) can be prepared by a variety of synthetic routes, including synthetic schemes described herein. These synthetic routes can be applied to large scale synthesis with appropriate adjustment of reaction sequence, reaction conditions, isolation/purification methods and choice of solvents which are environmentally friendly and cost-effective.

The term "therapeutically effective amount," as used herein refers to a total administered amount of an antibacterial compound that is effective to perform the function being sought by the researcher or clinician without unduly harming the tissues of the subject to which the agent is administered.

The term "subject," as used herein, refers to an animal, a plant, or a cell culture. In one embodiment, a subject is a human or other animal patient in need of antibacterial treatment.

The following abbreviations have the following meanings unless otherwise indicated. Abbreviations not defined below have their generally accepted meaning.

| | |
|---|---|
| Boc = | tert-butoxycarbonyl |
| Boc$_2$O = | di-tert-butyldicarbonate |
| CDI = | 1,1'-Carbonyldiimidazole |
| CFU = | colony-forming units |
| CLSI = | Clinical Laboratory Standards Institute |
| cSSSI = | complicated skin and skin structure infections |
| DCC = | N,N'-Dicyclohexylcarbodiimide |
| DCM = | dichloromethane |
| DIPEA = | diisopropylethylamine |
| DMF = | N,N-dimethylformamide |
| DMSO = | dimethyl sulfoxide |
| DPPA = | diphenylphosphoryl azide |
| EDCI = | 1-ethyl-3-(3'-dimethylaminopropyl)carbodiimide |
| HCl = | hydrochloride |
| EtOAc = | ethyl acetate |
| ESI-MS = | Electrospray ionization mass spectrometry |
| HAP = | Hospital-Acquired Pneumonia |
| HATU = | 2-(7-Aza-1H-benzotriazole-1-yl)-1,1,3,3-tetramethyluronium hexafluorophosphate |
| HCl = | hydrochloride |
| HOBT = | 1-hydroxybenzotrizole |
| hrs = | hours |
| HPLC = | High performance liquid chromatography |
| Hunig's base = | N,N-Diisopropylethylamine |
| mCPBA = | meta-Chloroperoxybenzoic acid |
| MIC = | Minimum inhibitory concentration |
| mL = | milliliter |
| MS = | Mass spectrometry |
| MRSA = | Methicillin-resistant *Staphylococcus aureus* |
| NCS = | N-Chlorosuccinimide |
| NMR = | nuclear magnetic resonance |
| Pa = | *Pseudomonas aeruginosa* |
| Pd$_2$(dba)$_3$ = | Tris(dibenzylideneacetone)dipalladium(0). |
| PdCl$_2$(dppf) = | Pd[1,1-bis (diphenylphosphino) ferrocene] dichloropalladium(II) |
| PFPOH = | pentafluorophenol |
| PMB = | para-methoxybenzyl |
| Prep = | Preparative |
| ppm = | parts per million |
| rt = | room temperature |
| THF = | tetrahydrofuran |
| TFA = | trifluoroacetic acid |
| TMS = | tetramethylsilane |
| TLC = | thin layer chromatography |
| VAP = | Ventilator-Associated Pneumonia |
| Xantphos = | 4,5-Bis(diphenylphosphino)-9,9-dimethylxanthene |

DETAILED DESCRIPTION

Figure 1:
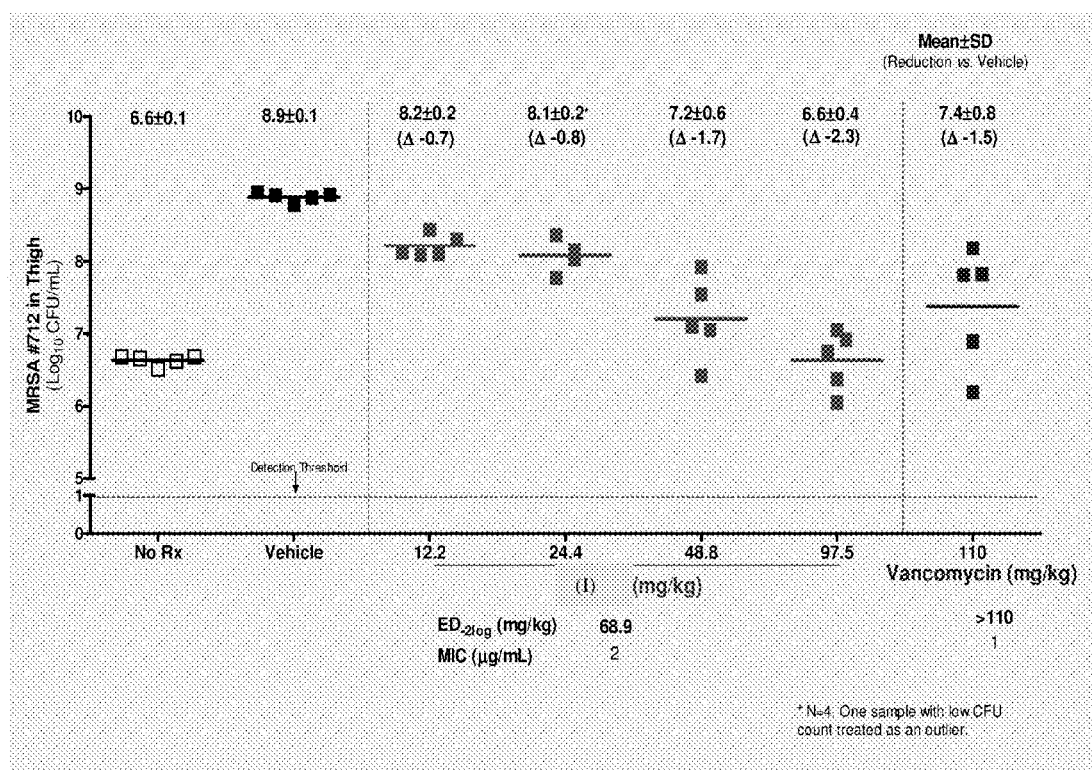
FIG. 1 depicts the efficacy of the compound of formula (I) against MRSA #712 thigh infection compared with vancomycin in neutropenic mice.

Provided herein is a compound of formula (I), or a pharmaceutically acceptable salt thereof, which is useful for treating bacterial infections. In particular, pharmaceutical compositions comprising the cephalosporin compound of formula (I) have a surprisingly broad spectrum of antibacterial activity and are useful to inhibit or kill various bacteria. For example, the antibacterial compound disclosed herein can be used in the manufacture of antibacterial medicaments and in methods for the treatment of bacterial infections, including treatment of both certain Gram-positive and Gram-negative bacterial infections. The cephalosporin compound of formula (I), or a pharmacologically acceptable salt thereof has the following structure:

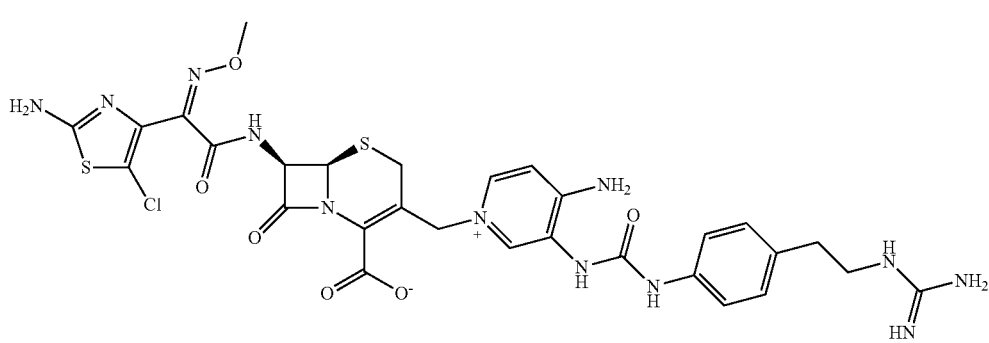

(I)

The compound of formula (I) has a MIC (measured by the method of Example 3) against *Pseudomonas aeruginosa* and methicillin-resistant *Staphylococcus aureus* (MRSA) of less than or equal to about 1-2 micrograms/mL.

Also included in formula (I) are zwitterionic forms containing an anionic carboxylic moiety and the cationic nitrogen in the pyridinium moiety. The imino group in the C-7 side chain position of the cephalosporin fused ring structure of formula (I) are shown in the "syn" (Z) configuration. The compound of formula (I) are preferably prepared as the syn-isomer (Z-isomer), or in mixtures comprising an amount of the syn-isomer (e.g., at least 90%) to provide a desired level of antibacterial activity, including compound of formula (I) that are syn isomers which are essentially free of the corresponding anti imino isomers.

The antibacterial properties of this compound based on minimum inhibitory concentrations (MICs) against certain *Staphylococcus* and *Pseudomonas* strains is listed in micrograms/mL which can be compared to comparable MICs measured for the compounds of Table 1.

The compound of formula (I) can be prepared from cephalosporin intermediate compound 4a as described in the Examples, or following literature procedures. For similar literature procedures, see, e.g., (a) Lattrell, R.; Blumbach, J.; Duerckheimer, W.; Fehlhaber, H. W.; Fleischmann, K.; Kirrstetter, R.; Mencke, B.; Scheunemann, K. H.; Schrinner, E.; et al. *J. of Antibiotics* 1988, 41, 1374. (b) Lattrell, R.; Blumbach, J.; Duerckheimer, W.; Fleischmann, K.; Kirrstetter, R.; Klesel, N.; Mencke, B.; Scheunemann, K. H.; Schwab, W.; et al. *J. of Antibiotics* 1988, 41, 1395. (c) Hanaki, H.; Yamazaki, H.; Harada, H.; Kubo, R.; Kobayashi, T.; Atsuda, K.; Sunakawa, K. *J. of Antibiotics* 2005, 58, 69-73; (d) Long, D. D.; Aggen, J. B.; Chinn, J.; Choi, S.-K.; Christensen, B. G.; Fatheree, P. R.; Green, D.; Hegde, S. S.; Judice, J. K.; Kaniga, K.; Krause, K. M.; Leadbetter, M.; Linsell, M. S.; Marquess, D. G.; Moran, E. J.; Nodwell, M. B.; Pace, J. L.; Trapp, S. G.; Turner, S. D. *J. of Antibiotics* 2008, 61, 603-614, all of which are incorporated by reference in their entireties.

4a

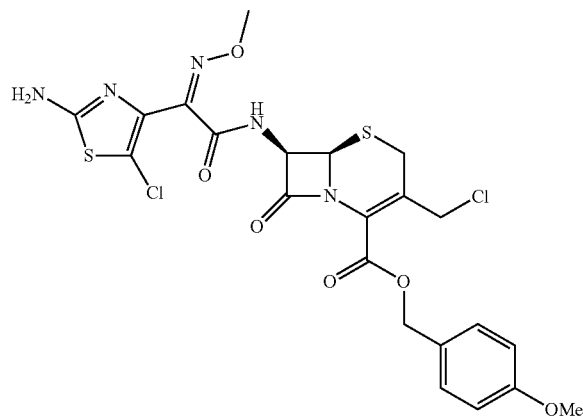

The antibiotic activity of the compound of formula (I) was measured against a variety of pathogenic microorganisms including Gram-positive and Gram-negative bacteria, including against *Staphylococcus* and *Pseudomonas* bacteria. Minimum inhibitory concentrations (MICs) for the compound of formula (I) against certain *Staphylococcus*, *Pseudomonas* and *pneumoniae* strains are listed in micrograms/mL in Table 2. The MICs were determined as described in Example 4.

Accordingly, the compound of formula (I) can be included in pharmaceutical antibacterial compositions and are useful both in the manufacture of medicaments for treating bacteria or bacterial infections, and in methods of treating conditions caused by bacteria such as infections.

Pharmaceutical antibacterial compositions can be formed by combining the compound of formula (I) or a pharmacologically acceptable salt thereof with a pharmacologically acceptable carrier suitable for delivery to a recipient subject (e.g., a human) in accordance with known methods of drug delivery. Antibacterial pharmaceutical compositions suitable for administration of one or more compound of formula (I) can be formulated. The compound of formula (I), and/or pharmacologically acceptable salts of formula (I) can be included in a pharmaceutical antibacterial composition along with one or more carriers.

Pharmaceutical compositions can be formed by combining the compound of formula (I) or a pharmacologically acceptable salt thereof with a pharmacologically acceptable carrier suitable for delivery to a recipient subject (e.g., a human) in accordance with known methods of drug delivery. Antibacterial pharmaceutical compositions suitable for administration of one or more compound of formula (I) can be formulated. The compound of formula (I), and/or pharmacologically acceptable salts of formula (I) can be included in a pharmaceutical antibacterial composition along with one or more carriers. Pharmaceutical preparations can be prepared in accordance with standard procedures and are administered at dosages that are selected to treat infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The compound of formula (I) can be formulated as a variety of salts to improve stability or toxicological properties of the compound, increase or decrease solubility, improve pharmacokinetic performance of the compound (e.g., $C_{max}$ or AUC measurements) or improve storage properties (e.g., to reduce hygroscopicity) of a pharmaceutical composition. As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S. M. Berge, et al. describes pharmacologically acceptable salts in *J. Pharm. Sci.*, 1977, 66:1-19. Pharmaceutically-acceptable salts of compound of formula (I) may be prepared by conventional means from the corresponding compound of the invention by treating, for example, the compound with the appropriate acid or base. Examples of publications describing the selection and formation of pharmacologically acceptable salts of medicinal compounds include Haynes, Delia A., et al., "Occurrence of Pharmacologically acceptable Anions and Cations in the Cambridge Structural Database," Journal of Pharmaceutical Sciences, v. 94, no. 10, 2111-2120 (October 2005), and Stahl, P H, et al., Eds., "Handbook of Pharmaceutical Salts: Properties, Selection and Use," Weinheim/Zurich, Wiley-VCH/VHCA.

A pharmaceutical composition can include a pharmaceutically-acceptable carrier and the compound of formula (I) and/or salts of formula (I). As used herein, the phrase "pharmaceutically-acceptable carrier" refers generally to solvents, dispersion media, excipients, coatings, matrices, stabilizers, buffers, absorption enhancers, adjuvents, controlled release media, and the like, that are compatible with an intended use, such as pharmaceutical administration. The use of such carriers for pharmaceutically active substances is well known in the art. The pharmaceutical compositions can be formulated for parenteral delivery, including intravenous, intramuscular, intraperetoneal, subcutaneous, intraocular, intrathecal, intra-articular, intra-synovial, cisternal, intrahepatic, intralesional and intracranial injection, infusion, and/or inhaled routes of administration for the therapeutic treatment of medical conditions, such as bacterial infections.

Pharmaceutical compositions for parenteral injection can comprise pharmaceutically-acceptable aqueous or nonaqueous solutions of antibacterial compound of formula (I) in addition to one or more of the following: pH buffered solutions, adjuvants (e.g. preservatives, wetting agents, emulsifying agents, and dispersing agents), liposomal formulations, nanoparticles, dispersions, suspensions or emulsions as well as sterile powders for reconstitution into sterile injectable solutions or dispersions just prior to use. For intravenous (IV) use, the pharmaceutical composition can include any of the commonly used intravenous fluids and administered by infusion, such as physiological saline or Ringer's solution.

The antibacterial compound of formula (I) disclosed herein, and pharmacologically acceptable salts thereof, including pharmaceutical compositions comprising these compounds, is useful in the manufacture of antibacterial pharmaceutical compositions, and treatment of bacteria. Significantly, the antibacterial compounds are useful in treating and eliminating a broad spectrum of bacterial pathogens, including both gram negative and gram positive bacterial infections. The antibacterial compound of formula (I) can be used in vivo, for example, to treat bacterial infections in a subject, as well as in vitro, for example to treat cells (e.g., bacteria) in culture to eliminate or reduce the level of bacterial contamination of a cell culture. In one embodiment, the compound of formula (I), or a pharmaceutical composition thereof, is administered to a cell culture, such as by administering in a nutrient medium. Methods of treating bacterial infections in subjects (e.g., humans and animals) can include the administration of a therapeutically effective amount of the compound of formula (I) or a pharmacologically acceptable salt thereof.

Methods of treatment of such infections include administering to a subject in need thereof a therapeutically effective amount of the compound of formula (I). The compound can be parenterally administered to a subject having or suspected to have a bacterial infection, such as a gram negative infection.

The antibacterial compound of formula (I) is preferably used in vivo to treat an infection in a subject by administering a therapeutically effective amount of the compound of formula (I) in a pharmaceutical composition. The method can comprise parenterally administering to a subject in need thereof a pharmaceutical composition comprising a therapeutically effective dose of at least one compound of formula (I). Pharmaceutical compositions include compositions comprising compound(s) of formula (I) in a dose sufficient to achieve the intended purpose, i.e., the treatment or prevent of infectious diseases. The amount and concentration of antibacterial compound of formula (I) in the pharmaceutical composition, as well as the quantity of the pharmaceutical composition administered to a subject, can be selected based on clinically relevant factors, such as medically relevant characteristics of the subject (e.g., age, weight, gender, other medical conditions, and the like), the solubility of the antibacterial compound in the pharmaceutical composition, the potency and activity of the antibacterial compound, any toxicity associated with the pharmaceutical composition dose and method of administration, and the manner of administration of the pharmaceutical composition.

A pharmaceutical composition comprising a therapeutically effective dose of the compound of formula (I) can be administered intravenously to a patient for treatment of gram negative infections in a clinically safe and effective manner, including one or more separate administrations of the composition. The total daily dose of the compound of formula (I) can be about 2.0 mg/kg/day to about 50 mg/kg/day of all compound of formula (I) administered intravenously to a subject one to three times a day (e.g., QD, BID or TID). The amount per administered dose or the total amount administered will depend on such factors as the nature and severity of the infection, the age and general health of the patient, the tolerance of the patient to the compound and the microorganism or microorganisms involved in the infection. The total amount of the pharmaceutical composition administered can be selected to be therapeutically effective.

In particular, the pharmaceutical compositions comprising the compound of formula (I) can be used to treat a subject having a bacterial infection in which the infection is caused or exacerbated by a gram-negative bacteria. A method of treating a bacterial infection in a host can include administering to an infected host a pharmaceutical composition comprising a therapeutically effective dose (e.g., an antibacterially effective amount) of the compound of formula (I), or a pharmacologically acceptable salt thereof.

The pharmaceutical composition and/or compound(s) of formula (I) can be administered to treat a bacterial infection or population in vitro (e.g., a bacterial colony on a surface outside the body) or in vivo (e.g., within an infected host). The bacterial infection or population can include Gram-negative and/or Gram-positive bacteria. For example, the Gram-negative bacteria can comprise *Pseudomonas aeruginosa* and the Gram-positive bacteria can include *Staphylococcus aureus*. The bacteria can form an infection present in vitro (e.g., a bacterial colony or sample), or in vivo (e.g., an infected host subject). For instance, the bacterial infection can be identified as a methicillin-resistant *Staphylococcal* infection. Preferably, the antibacterially effective dose and therapeutically effective amount of the compound(s) of Formula (I) can be effective in killing both a *Pseudomonas aeruginosa* bacteria and a MRSA bacteria with a MIC that is less than the comparable value for a compound in Table 1, and/or independent MIC values measured according to Example 3 that is not more than about 4 micrograms/mL (e.g., including values of about 3.5, 3.0, 2.5, 2.0, 1.5, 1.0, 0.5 micrograms/mL or lower) independently measured against each of *Pseudomonas aeruginosa* bacteria and methicillin-resistant *Staphylococcal* bacteria.

A pharmaceutical composition containing a therapeutically effective amount of the compound of formula (I) can be administered to a patient presenting symptoms of an infection. The compounds of this invention can be used to treat infections of cSSSI and HAP/VAP in adults or children. In particular methicillin resistant *Staphylococcus aureus* infections and/or *Pseudomonas* infections may be treated with the compound of formula (I). Other representative types of infections or bacteria-related medical conditions which can be treated or prevented with pharmaceutical compositions comprising antibacterial compound of formula (I) include, but are not limited to, skin and skin structure infections, urinary tract infections, pneumonia, endocarditis, catheter-related blood stream infections, osteomyelitis, and the like. In treating such conditions, the patient may treated with the pharmaceutical compositions comprising the compound of formula (I) upon presenting symptoms consistent with a bacterial infection. The pharmaceutical compositions may be administered prior to or after identifying the types of bacteria present in the patient.

EXAMPLES

The specific examples which follow illustrate the synthesis of certain compounds used in the preparation of the compound of formula (I). Further, the disclosure includes variations of the methods described herein to produce the compound of formula (I) that would be understood by one skilled in the art based on the instant disclosure.

All temperatures are understood to be in Centigrade (C) when not specified. The nuclear magnetic resonance (NMR) spectral characteristics refer to chemical shifts (γ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), singlet (s), multiplet (m), doublet (d), quartet (q), doublet of doublet (dd), doublet of triplet (dt), and doublet of quartet (dq). The solvents employed for taking NMR spectra are DMSO-d6 (perdeuterodimethysulfoxide), D$_2$O (deuterated water), CDCl$_3$ (deuterochloroform) and other conventional deuterated solvents. The prep-HPLC conditions are: Waters SunFire® C18 (30×100 mm, 5 μm) column; flow rate: 50 mL/min, UV or Mass-triggered fraction collection; sample loading: each injection loading varied from 30-80 mg depending for different crude samples depending on their solubility and purity profiles; solvent system: solvent A: water with 0.5% formic acid, solvent B: acetonitrile with 0.5% formic acid.

Example 1

Synthesis of (6R,7R)-4-methoxybenzyl 7-((Z)-2-(2-amino-5-chlorothiazol-4-yl)-2-(methoxyimino)acetamido)-3-(chloromethyl)-8-oxo-5-thia-1-azabicyclo [4.2.0]oct-2-ene-2-carboxylate (intermediate compound 4a)

4a

Step 1: Preparation of (6R,7R)-4-methoxybenzyl 7-amino-3-(chloromethyl)-8-oxo-5-thia-1-azabicyclo [4.2.0]oct-2-ene-2-carboxylate

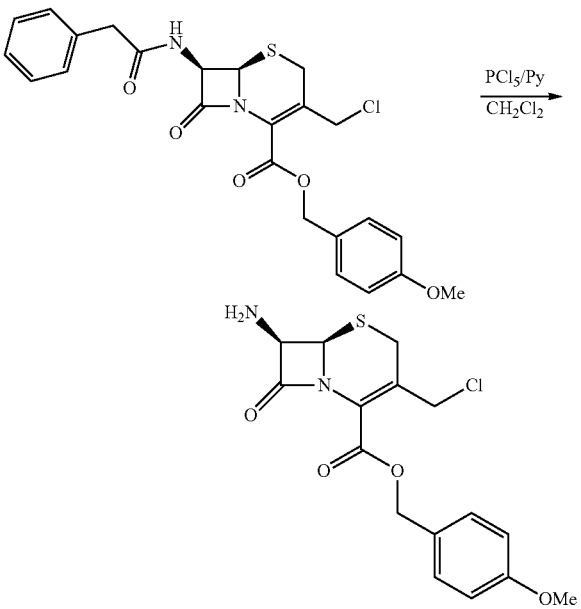

To a suspension of PCl$_5$ (3.21 g) in dry DCM (50 mL) at 0° C. was added anhydrous pyridine (1.24 mL) and the resulting white suspension was stirred for 0.5 h. 7-Phenylacetamido-3-chloromethyl-3-cephem-4-carboxylic acid p-methoxy benzyl ester (5.0 g) was added. After stirring at 0° C. for additional 2 h, the reaction mixture was cooled to −40° C. and methanol (15 mL) was added dropwise. The stirring was continued at −30° C. for additional 0.5 h, and the reaction mixture was then concentrated. To the residue were added water (5 mL), EtOAc (20 mL) and diethyl ether (200 mL), and the mixture was stirred at 0° C. until precipitation formed. The yellow precipitate was collected by filtration, rinsed with diethyl ether and then 20% DCM in diethyl ether, and dried under high vacuum. The resulting light yellow solid was used directly in step 3. ESI-MS (EI$^+$, m/z): 369.05.

Step 2: Synthesis of (Z)-2-(2-amino-5-chlorothiazol-4-yl)-2-(methoxyimino)acetic acid

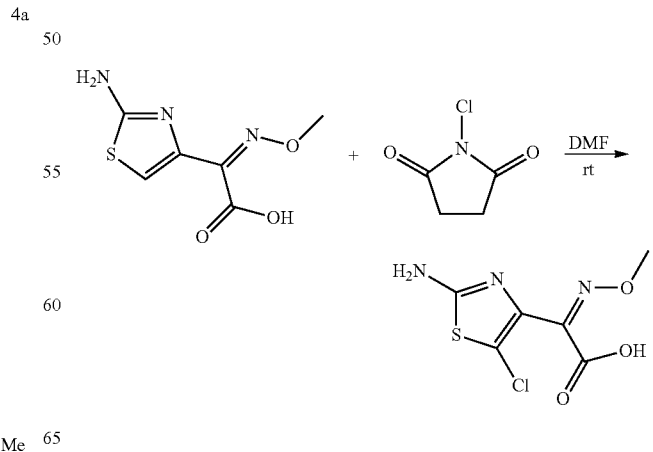

To a solution of (Z)-2-(2-aminothiazol-4-yl)-2-(methoxyimino)acetic acid (15.0 g) in anhydrous DMF (150 mL) was added NCS (11.95 g) and the mixture was stirred at rt for 2-3 hrs. The reaction mixture was concentrated to remove most of the DMF. The resulting oil was added dropwise to DCM (~600 mL) at 0° C. with stirring. Solid precipitation was collected by filtration, rinsed with DCM and dried under high vacuum to provide a brownish solid (11.8 g, 67%). ESI-MS (EI+, m/z): 236.0. $^1$H NMR (300 MHz, DMSO-d6) δ 7.60 (br s, 2H), 3.88 (s, 3H).

Step 3: Synthesis of Compound 4a Via EDCl Coupling

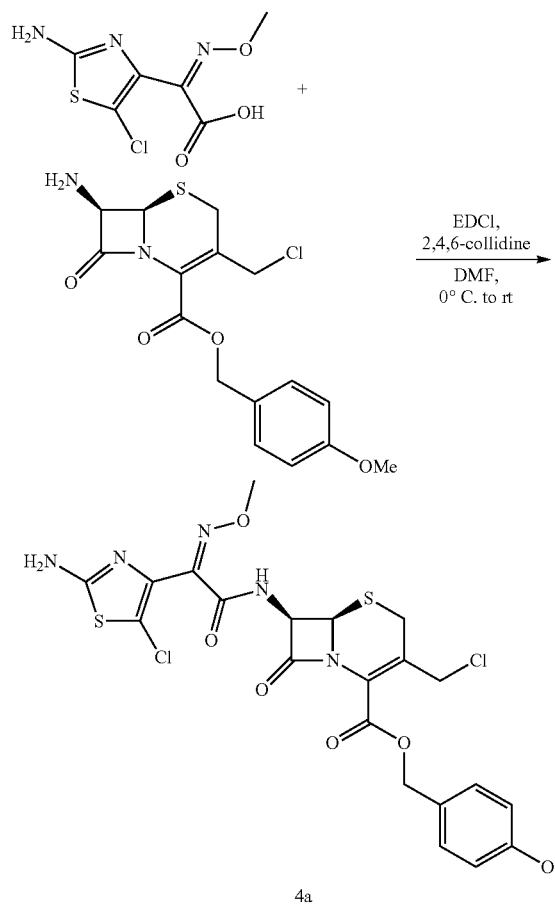

4a

To a solution of (6R,7R)-4-methoxybenzyl 7-amino-3-(chloromethyl)-8-oxo-5-thia-1-azabicyclo[4.2.0]oct-2-ene-2-carboxylate (6.8 g) in dry DMF (60 mL) was added (Z)-2-(2-amino-5-chlorothiazol-4-yl)-2-(methoxyimino)acetic acid (4.17 g). The mixture was cooled to 0° C., then 2,4,6-collidine (2.3 g) and EDCl (3.4 g) were added sequentially. After 2 hrs, the solution was poured into cold water and filtered. The solid was rinsed with water, dried under high vacuum and purified by silica gel chromatography (DCM:EtOAc=3:1) to afford 4a (5.0 g, 57%). ESI-MS (EI+, m/z): 586.04; $^1$H NMR (400 MHz, D$_2$O) δ 9.60 (d, J=8.8 Hz, 1H), 7.39 (br s, 2H), 7.36 (d, J=8.4 Hz, 2H), 6.93 (d, J=8.4 Hz, 2H), 5.83 (dd, J=8.8, 5.2 Hz, 1H), 5.24 (d, J=12.0 Hz, 1H), 5.19 (d, J=5.2 Hz, 1H), 5.18 (d, J=12.0 Hz, 1H), 4.54 (d, J=11.4 Hz, 1H), 4.46 (d, J=11.4 Hz, 1H), 3.86 (s, 3H), 3.76 (s, 3H), 3.70 (d, J=18.0 Hz, 1H), 3.54 (d, J=18.0 Hz, 1H).

Example 2

Synthesis of tert-butyl 1-(pyridin-4-yl)hydrazinecarboxylate

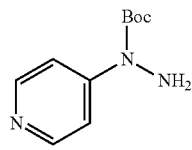

A mixture of 4-bromo-pyridine hydrochloride salt (8.0 g), tert-butyl hydrazinecarboxylate (10.87 g), CuI (784 mg), L-4-hydroxyproline (1.08 g) and Cs$_2$CO$_3$ (33.50 g) in dry DMSO (41 mL) under N$_2$ was heated at 80° C. with efficient stirring for 5-6 hrs. After cooled to rt, the reaction mixture was diluted with EtOAc (150 mL) and saturated NH$_4$Cl (150 mL). The organic layer was separated and the aqueous was extracted with EtOAc (3×150 mL). The combined organic layers were washed with brine (50 mL), dried (Na$_2$SO$_4$) and concentrated. The residue was purified by silica gel column chromatography (DCM to 10% MeOH/DCM gradient) to provide the title compound (3.4 g, 40%). ESI-MS (EI+, m/z): 210.0 [M+H]+. $^1$H NMR (300 MHz, DMSO) δ 8.38 (d, J=4.9 Hz, 2H), 7.64 (d, J=6.4 Hz, 2H), 5.12 (s, 2H), 3.34 (s, 1H), 1.51 (s, 9H).

Example 3

Biological Activity Assay (A)

As shown in Table 1, the antibacterial activity of the comparator compounds was demonstrated by the minimum inhibitory concentrations (MIC) of the compounds against various bacteria measured by using the broth microdilution method performed according to Clinical and Laboratory Standards Institute (CLSI) guidelines with modifications as described below (CLSI guidelines can be derived from the CLSI document M7-A8 published in January 2009: "Methods for Dilution Antimicrobial Susceptibility Tests for Bacteria That Grow Aerobically; Approved Standard-Eighth Edition").

To prepare for MIC testing, individual colonies were isolated by streaking frozen glycerol material containing *Staphylococcus* or *Pseudomonas* spp. onto rich, non-selective, tryptic soy agar containing 5% sheep's blood (TSAB), and incubated at 37° C. for 18-24 hrs.

On the day of testing, primary cultures were started by scraping off 5-10 colonies from the TSAB plates. The material was suspended in ~5 mL of cation adjusted Mueller Hinton Broth (CAMHB) in 14 mL culture tubes and incubated at 37° C. with aeration (200 rpm) for ~2 hrs until the OD600 was ≥0.1.

Inoculum cultures were prepared by standardizing the primary cultures to OD600=0.1 and then adding 20 µL of the adjusted primary culture per 1 mL CAMHB for *Pseudomonas* and CAMHB plus 4% NaCl for MRSA so that the final inoculum density was ~10$^5$ colony forming units per milliliter. Diluted inoculum cultures were used to inoculate 50 µL per well in 96 well broth microdilution assay plates. 50 µL of CAMHB that contained compound concentrations ranging from 64-0.06 μg/mL in two-fold dilutions was also added to the broth microdilution assay plates for a final volume 100 μL per well, therefore final culture OD600 was approximately 0.001 and the final NaCl concentration for the MRSA strain was 2%.

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. MIC values were defined as the lowest concentration producing no visible turbidity.

Example 4

Biological Activity Assay (B)

As shown in Table 2, the efficacy of the compound of formula (I) was evaluated in mouse septicemia, thigh and lung infection models against multiple strains of MRSA, ceftazidime-susceptible and -resistant *Pseudomonas aeruginosa* and ceftazidime-resistant *Klebsiella pneumoniae* and compared with standard antibiotic treatment.

Figure 2:
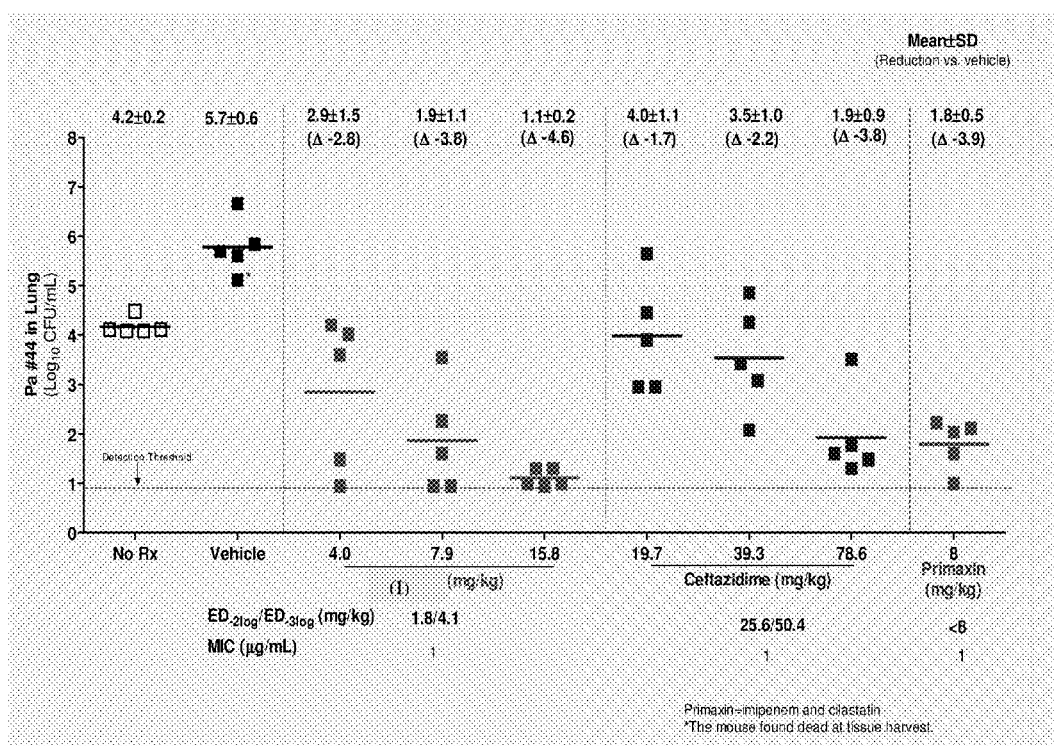
FIG. 2 depicts the efficacy of the compound of formula (I) against ceftazidime-susceptible *pseudomonas aeruginosa* #44 (ATCC#27853) lung infection compared with ceftazidime and primaxin in neutropenic mice.
Figure 3:
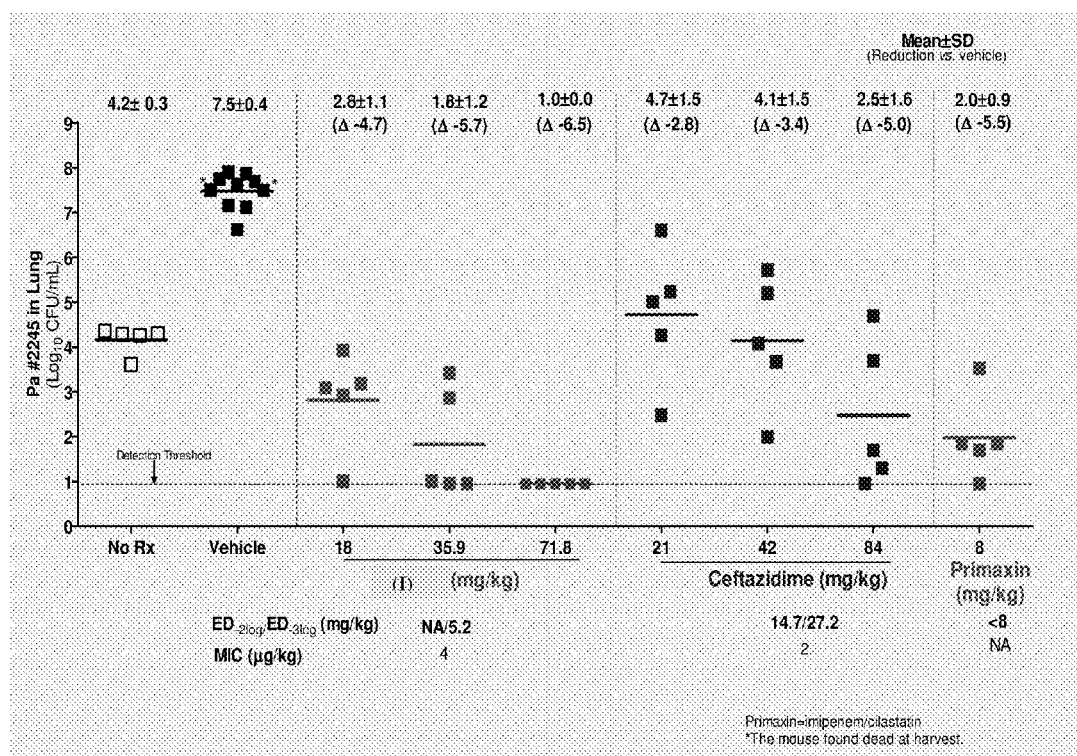
FIG. 3 depicts the efficacy of the compound of formula (I) against ceftazidime-susceptible *pseudomonas aeruginosa* #2245 lung infection compared with ceftazidime and primaxin in neutropenic mice.
Figure 4:
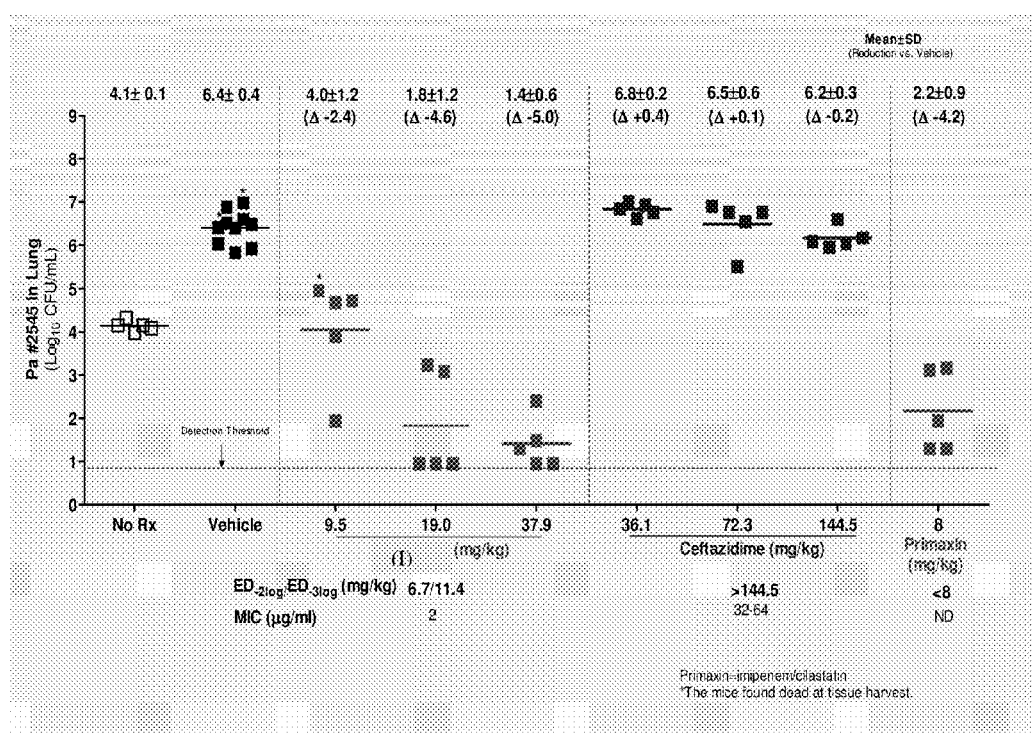
FIG. 4 depicts the efficacy of the compound of formula (I) against ceftazidime-resistant *pseudomonas aeruginosa* #2545 lung infection compared with ceftazidime and primaxin in neutropenic mice.

I. Summary
  The compound of formula (I) is a novel broad spectrum cephalosporin with potent in vitro activities against G(+) and G(−) bacteria including MRSA and *Pseudomonas aeruginosa* (Pa). In vivo efficacy of (I) was evaluated against strains of MRSA, and ceftazidime-resistant Pa and *Klebsiella* pneumonia (Kpn) in mouse septicemia, thigh and lung infections. Septicemia: CD-1 mice received lethal bacterial inocula IP, followed by 2 doses of antibiotics SC at 1 and 6 hrs post-inoculation. Dose calculated to protect 50% of the mice ($PD_{50}$) was derived based on probit analysis of percentage survival. Thigh and lung infections: Thighs or lungs of neutropenic mice were inoculated with MRSA or Pa. Two treatment doses were given SC at 1 and 6 hrs post-inoculation. Tissues were harvested at ~24 hrs post-inoculation and bacterial burdens quantified. Efficacious dose resulting in a 2-log bacterial CFU reduction ($ED_{-2\,log}$) compared with vehicle-treated mice was calculated. (I) demonstrated potent in vivo activity against several drug-resistant strains. Its in vivo potency against a clinical isolate of MRSA was comparable to vancomycin and ceftaroline. (I) also had good activities against ceftazidime-resistant Pa and Kpn. (I) exhibits excellent in vivo efficacy against infections caused by MRSA, and ceftazidime-resistant Pa and Kpn in mice.
II. Methods
  A. Animals: Six week-old, specific pathogen free, female CD-1 mice purchased from Charles River Laboratories (Wilmington, Mass.) were used for all studies after acclimation in Cubist animal facility. All animal procedures were approved by the Cubist Institutional Animal Care and Use Committee.
  B. Bacteria and In Vitro Susceptibility Testing: MRSA #712, *Pseudomonas aeruginosa* #2245 and #2545, and *Klebsiella pneumoniae* #573 are clinical isolates; *Pseudomonas aeruginosa* #44 is an ATCC strain (ATCC#27853). MIC was determined in MHB by standard CLSI microdilution. MICs of individual strains are shown in Table 2 and FIGS. 1-4.
  C. Comparator Antibiotics Used in Animal Studies: Vancomycin hydrochloride USP was purchased from Hospira (Lake Forest, Ill.); ceftazidime hydrate from Sigma; Primaxin (imipenem and cilastatin) from Merck; ceftaroline was synthesized at a CRO.
  D. Mouse Septicemia: Mice received lethal inocula of bacteria in 6% hog gastric mucin intraperitoneally (IP), followed by two treatment doses of antibiotics via subcutaneous (SC) administration at 1 and 6 hrs post-inoculation. The survival of animals was recorded daily for 7 days. The antibiotic dose calculated to protect 50% of the mice ($PD_{50}$) was derived based on probit analysis of percentage survival.
  E. Mouse Thigh and Lung Infections: Mice were rendered neutropenic by two IP injections of cyclophosphamide 4 days (150 mg/kg) and 1 day (100 mg/kg) before bacterial inoculation. Thigh or lung infection was induced by an intramuscular injection of 0.2 mL or intranasal inoculation of 0.1 mL inoculum preparation from an overnight bacterial culture into left thigh or nares. Tissues from one group of mice receiving no treatment (No Rx) were harvested at 1 hr for determination of baseline of bacterial burden. The remaining mice received two treatment doses of vehicles or antibiotics given SC at 1 and 6 hrs post-inoculation. Tissues from the treated mice were harvested at ~24 hrs post-inoculation. Tissue bacterial burdens were quantified by serial dilution and spiral plating of homogenates. Doses of (I) were confirmed analytically. The efficacious dose resulting in a 2-log or a 3-log bacterial CFU reduction ($ED_{-2\,log}$ or $ED_{-3\,log}$) as compared with vehicle-treated mice at 24 h was derived by linear regression analysis.
III. Results
  A. (I) displayed potent efficacy in all systemic infection models. Its $PD_{50}$ value of 2.0±0.3 mg/kg against MRSA #712 septicemia was comparable to vancomycin and ceftaroline. (I) was significantly more potent in vivo than ceftazidime against the CLSI reference strain of *Pseudomonas aeruginosa* #44 ($PD_{50}$: 5.3±0.7 vs. 33.9±7.4 mg/kg, respectively. (I) demonstrated good in vivo potency against ceftazidime-resistant *Pseudomonas aeruginosa* #2545 and *Klebsiella pneumoniae* #573 systemic infections (Table 1).
  B. (I) led to a dose-dependent reduction of MRSA #712 burden in the thigh vs. vehicle controls with an $ED_{-2\,log}$ of 68.9 mg/kg (FIG. 1). In contrast, vancomycin at 110 mg/kg SC resulted in a smaller reduction in bacterial CFU (~1.5 log). The vancomycin dose was chosen based on PK studies showing that the plasma exposure at this dose level in mice (data on file) was approximately equivalent to that in humans.
  C. (I) showed marked efficacy against ceftazidime-susceptible *Pseudomonas aeruginosa* #44 and #2245 lung infections with $ED_{-3\,log}$ values of 4.1 and 5.2 mg/kg, respectively. Ceftazidime had higher $ED_{-3\,log}$ values of 50.4 and 27.2 mg/kg, respectively (FIGS. 2 and 3). Bacterial burden in the lung at the highest doses of (I) in these two studies approached the lower limit of detection of the assay.
  D. (I) was efficacious against a ceftazidime-resistant *Pseudomonas aeruginosa* #2545 lung infection (FIG. 4). Its $ED_{-3\,log}$ value was 11.4 mg/kg. In contrast, ceftazidime up to 144.5 mg/kg had minimal impact on the bacterial burden in the lung.
IV. Conclusions
  A. (I) exhibited excellent efficacy against systemic and tissue infections caused by MRSA and ceftazidime-resistant *Pseudomonas aeruginosa* and *Klebsiella pneumoniae* in mice.

B. In vivo efficacy of (I) against a clinical isolate of MRSA was comparable to both vancomycin and ceftaroline in the thigh infection model in neutropenic mice.

C. (I) appeared more efficacious than ceftazidime in lung infections caused by ceftazidime-susceptible *Pseudomonas* strains in neutropenic mice.

D. (I) maintained potent activity vs. a mouse lung infection induced by a ceftazidime-resistant *Pseudomonas* isolate.

Example 5

Biological Activity Assay (C)

I. Summary

The $3^{rd}$ and $4^{th}$ generation cephalosporins bearing pyridinium or quaternary ammonium groups at the C-3' position, such as ceftazidime (CAZ) and cefepime, have potent activity against Gram-negative bacteria including *Pseudomonas aeruginosa* (Pa). However, their activity against Gram-positive bacteria such as methicillin-resistant *Staphylococcus aureus* (MRSA) is weak, limiting their clinical usefulness for empiric treatment. Thus, a broad spectrum cephalosporin with improved activity against both Pa and MRSA would be of particular interest. The compound of formula (I) demonstrated potent in vitro activity and broad spectrum coverage against both Gram-positive and Gram-negative bacteria, including MRSA and Pa. The $MIC_{90}$ of the compound of formula (I) is equivalent to that of CAZ against Pa, and comparable to those of ceftaroline and vancomycin against MRSA. The compound of formula (I) has potent antibacterial activity against serious bacterial pathogens such as Pa and MRSA.

II. Biological Activity Assay

A. The antibacterial activity of the compounds in Table 3 were demonstrated by the minimum inhibitory concentrations (MIC) using the broth microdilution method performed according to Clinical and Laboratory Standards Institute (CLSI) guidelines with minor modifications.

B. MIC values were defined as the lowest concentration producing no visible turbidity. $MIC_{90}$ values were defined as the concentration required to inhibit growth of 90% of the strains tested.

C. SAR was performed using the following isolates: Sa399 (ATCC43300, MRSA), Sa1721 (NARSA NRS384, MRSA USA 300), Pa44 (ATCC27853), and 4 clinical isolates (Pa2241, Pa2086 (mucoid strain), Pa2694 and Pa2698).

Figure 6:
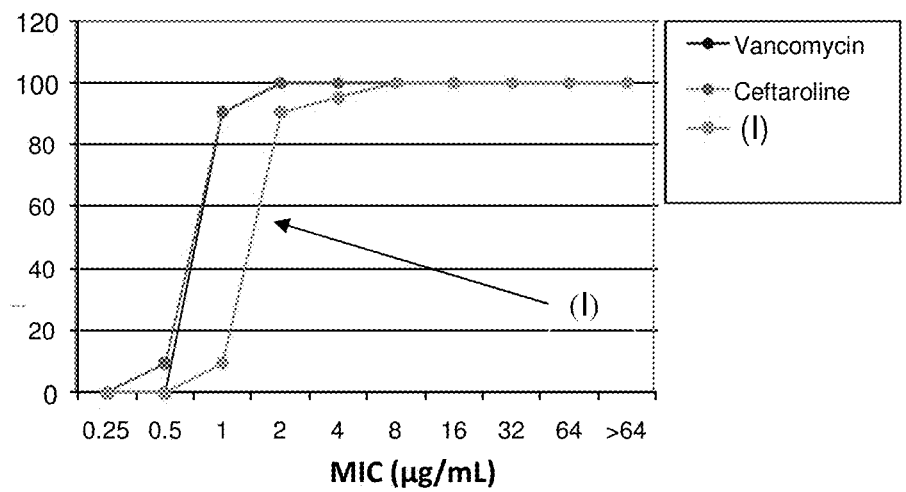
FIG. 6 depicts the distribution of MICs of the compound of formula (I) against MRSA and Pa strains with comparators.
Figure 6:
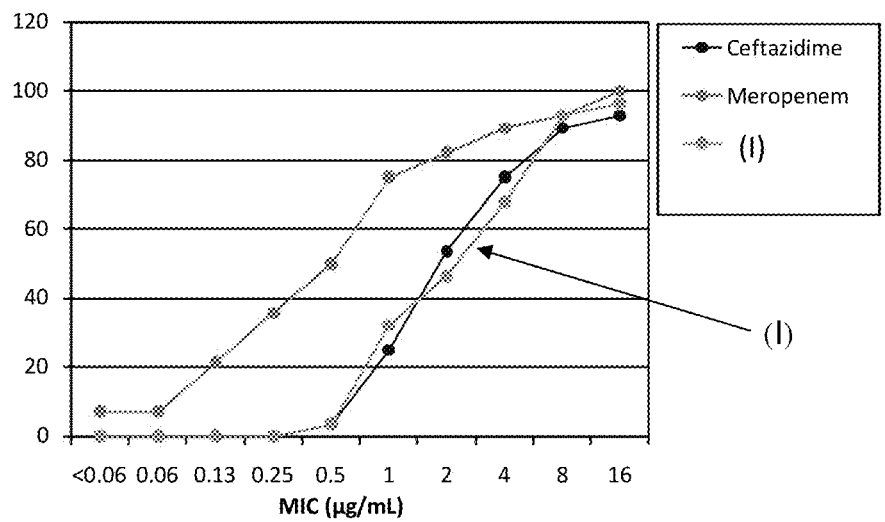

D. The in vitro antibacterial activity of the compound of formula (I) was further evaluated in an expanded MRSA and Pa MIC panel (see Table 4 and FIG. 6).

III. Efficacy Study

A. A mouse systemic infection model was used to determine in vivo efficacy. An overnight culture of *S. aureus* 712 (MRSA, clinical isolate) or Pa44 (ATCC 27853) suspended in 6% hog gastric mucin to prepare the inoculum. Mice were challenged via intraperitoneal (IP) inoculation of the bacteria with a lethal dose of $2\times10^7$ CFU/mouse.

B. Mice were given subcutaneous (SC) doses of test compound or saline at 1 and 6 hours after bacterial inoculation. The dose that protected 50% of the mice ($PD_{50}$) was calculated by probit analysis based on percentage of mice surviving for 7 days post-inoculation.

C. Compounds were formulated in a dosing solution of saline or D5W.

Example 6

Synthesis of (I)

Figure 5:
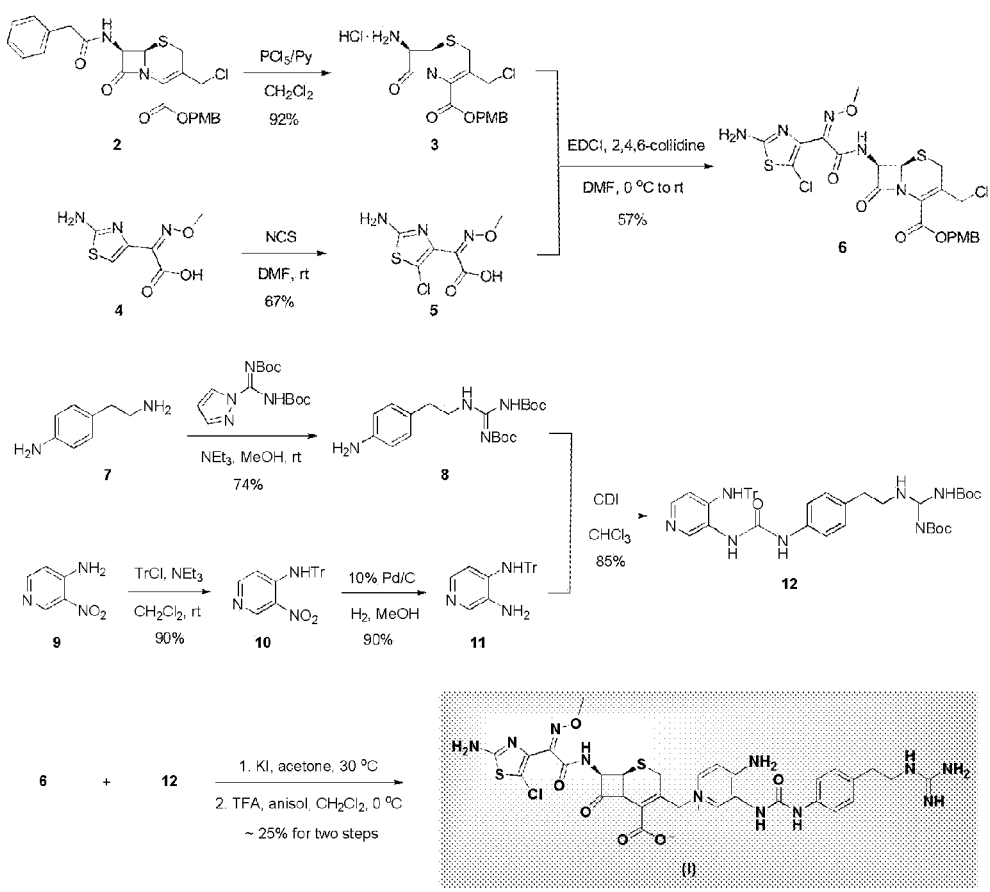
FIG. 5 depicts the synthesis of the compound of formula (I).

As shown in FIG. 5, cephalosporin core intermediate 6 was synthesized by amide coupling of 7-aminocephalosporin derivative 3 and chloroaminothiazole derivative 5. Urea tail 12 was prepared by CDI mediated urea formation of aniline derivative 8 and aminopyridine derivative 11. Coupling of intermediate 6 and urea tail 12, followed by global deprotection using TFA/anisol provided the final product (I), which was purified by reverse phase HPLC using 0.1% formic acid buffer in water/acetonitrile.

The examples and illustrative embodiments described herein are provided by way of illustration, and do not constitute additional limitations on the scope of the claims. While some embodiments have been shown and described in the instant specification, the specification as ready by one of ordinary skill in the relevant arts also discloses various modifications and substitutions of embodiments explicitly disclosed herein. The exemplary embodiments from the specification are not provided to read additional limitations into the claims.

TABLE 1

MICs (µg/mL) of Comparator Compounds

| Compound | Description | Structure | Sa399 (MRSA) | Pa44 (WT Pa) |
|---|---|---|---|---|
| XX-990,020 | Ceftazidime | 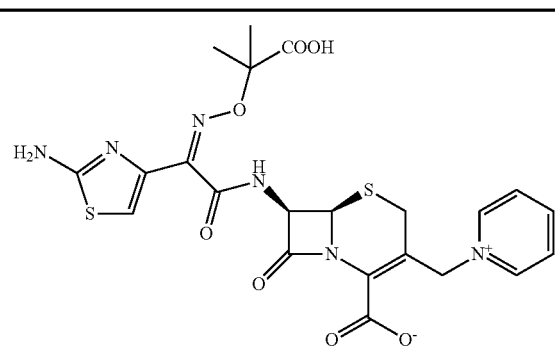 | C | A |

TABLE 1-continued
MICs (μg/mL) of Comparator Compounds
| Compound | Description | Structure | Sa399 (MRSA) | Pa44 (WT Pa) |
|---|---|---|---|---|
| XX-184,831 | Cefpirome | 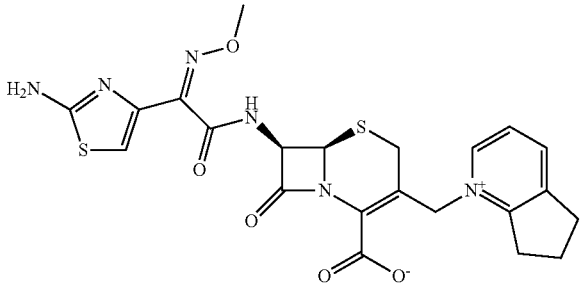 [SMILES: CO/N=C(\C(=O)N[C@@H]1C(=O)N2C(C(=O)[O-])=C(C[n+]3cccc4c3CCC4)CS[C@H]12)c1csc(N)n1] | B | A |
| Cefepime | Cefepime | 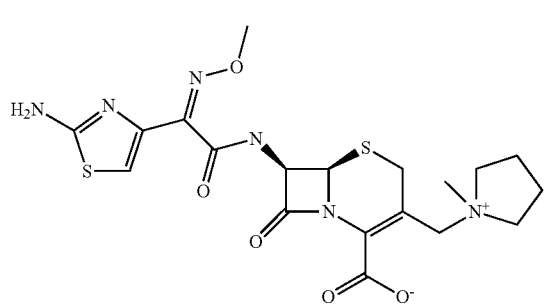 [SMILES: CO/N=C(\C(=O)N[C@@H]1C(=O)N2C(C(=O)[O-])=C(C[N+]3(C)CCCC3)CS[C@H]12)c1csc(N)n1] | C | A |
| 1-1 | | 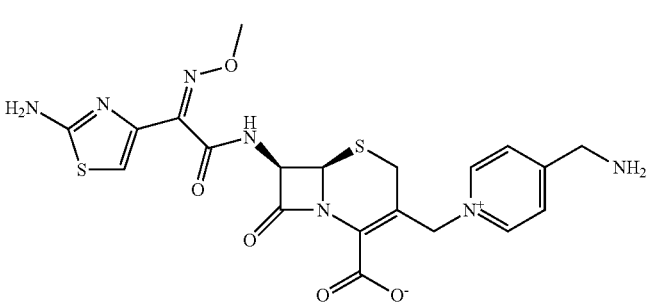 [SMILES: CO/N=C(\C(=O)N[C@@H]1C(=O)N2C(C(=O)[O-])=C(C[n+]3ccc(CN)cc3)CS[C@H]12)c1csc(N)n1] | C | A |
| 1-2 | | 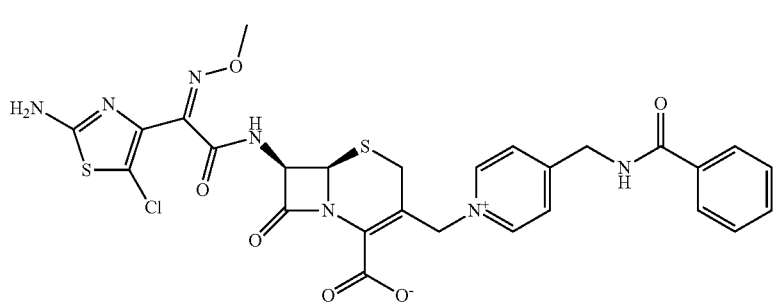 [SMILES: CO/N=C(\C(=O)N[C@@H]1C(=O)N2C(C(=O)[O-])=C(C[n+]3ccc(CNC(=O)c4ccccc4)cc3)CS[C@H]12)c1nc(N)sc1Cl] | A | C |
| 1-3 | | 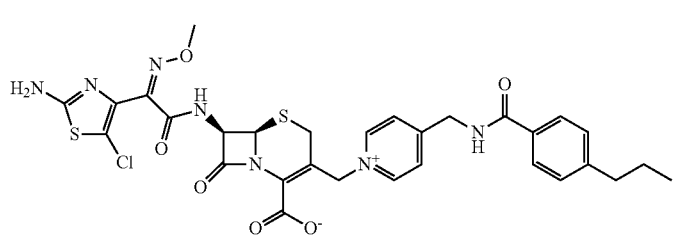 [SMILES: CCCc1ccc(C(=O)NCc2cc[n+](CC3=C(C(=O)[O-])N4C(=O)[C@@H](NC(=O)/C(=N\OC)c5nc(N)sc5Cl)[C@H]4SC3)cc2)cc1] | B | C |

TABLE 1-continued

MICs (μg/mL) of Comparator Compounds

| Compound | Description | Structure | Sa399 (MRSA) | Pa44 (WT Pa) |
|---|---|---|---|---|
| 1-4 | | 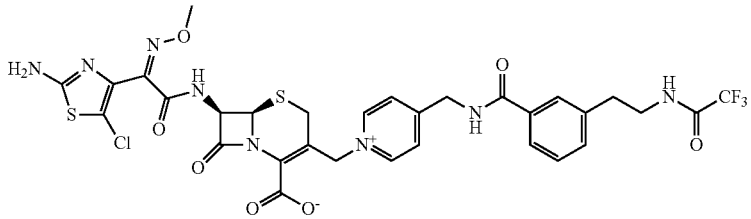 [SMILES: CO/N=C(\C(=O)N[C@@H]1C(=O)N2C(C(=O)[O-])=C(C[n+]3ccc(CNC(=O)c4cccc(CCNC(=O)C(F)(F)F)c4)cc3)CS[C@H]12)c1nc(N)sc1Cl] | B | C |

(A: ≤4; B: 8-16; C: >16)

TABLE 2

PD50 and ED−2log of (I) in Mouse Systemic, Thigh and Lung Infections

| Bacterial Strain | (I) or Comparator | Septicemia PD$_{50}$ (± SE, mg/kg) | Thigh (T) and Lung (L) ED$_{-2log}$(mg/kg) | MIC (μg/mL) |
|---|---|---|---|---|
| MRSA #712 | (I) | 2.0 ± 0.3 | 68.9 (T) | 2 |
| | Ceftaroline | 1 0 ± 0.1 | ND | 1 |
| | Vancomyon | 2.0 ± 1.3 | >110 (T) | 1 |
| Pa #44 | (I) | 5.3 ± 0.7 | 1.8 (L) | 1 |
| {ATCC27853} | Ceftazidime | 33.9 ± 7.4 | 25.6 (L) | 1 |
| | Primaxin | <2 | <8 (L) | 1 |
| Pa #2545 | (I) | <10.4 | 6.7 (L) | 2 |
| | Ceftazidime | >140.5 | >144.5 (L) | 32-64 |
| | Primaxin | >4 | <8(L) | ND |
| Kpn #573 | (I) | <1.3 | ND | 1 |
| | Ceftazidime | 50.3 ± 8.4 | ND | 256 |
| | Primaxin | 1.0 ± 0.6 | ND | 0.12 |

TABLE 3

In vitro activities of the compound of formula (I) and comparators

| | MIC (μg/ml) | | | | | | |
|---|---|---|---|---|---|---|---|
| | MRSA | | Pseudomonas | | | | |
| Compound | Sa399 | Sa1721 | Pa44 | Pa2241 | Pa2086 | Pa2694 | Pa2698 |
| Ceftaroline | 0.5 | 2 | 8 | 16 | 16 | >64 | >64 |
| Ceftazidime | 64 | >64 | 2 | 2 | 2 | 8 | 8 |
| (I) | 2 | 8 | 2 | 1 | 8 | 8 | 8 |

TABLE 4

MIC$_{90}$ of the compound of formula (I) against MRSA and Pa with comparators

| | MIC$_{90}$(μg/mL) | |
|---|---|---|
| Compound | MRSA (n = 21) | Pseudomonas aeruginosa (n = 100) |
| Ceftazidime | — | 8 |
| Meropenem | — | 4 |
| Ceftaroline | 1 | — |
| Vancomycin | 1 | — |
| (I) | 2 | 8 |

We claim:

1. The compound of formula (I), or a pharmacologically acceptable salt thereof:

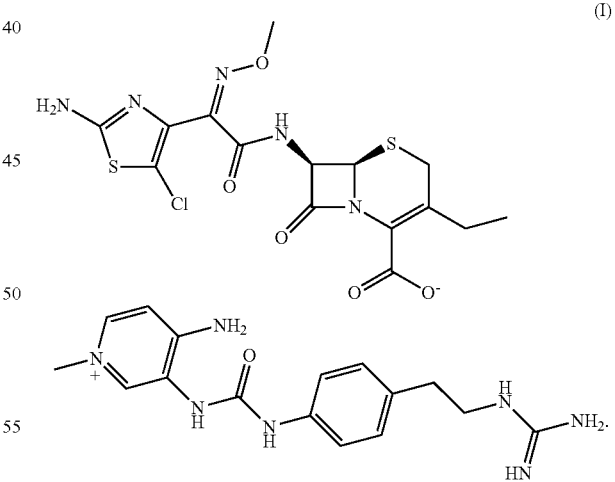

(I)

2. A pharmaceutical composition comprising a therapeutically effective amount of the compound of claim 1, or a pharmacologically acceptable salt thereof.

3. A method of treating a bacterial infection in a host comprising administering to an infected host a pharmaceutical composition comprising an antibacterially effective amount of a compound of claim 1 or a composition of claim 2.

4. The method of claim 3, wherein the bacterial infection is caused by a Gram-negative and/or a Gram-positive bacteria.

5. The method of claim 4, wherein the Gram-negative bacteria is *Pseudomonas aeruginosa* and the Gram-positive bacteria is *Staphylococcus aureus*.

6. A method of treating a methicillin-resistant *Staphylococcal* infection, comprising parenterally administering to a patient in need thereof a pharmaceutical composition comprising a carrier and a therapeutically effective amount of a compound of claim 1, or a pharmacologically acceptable salt thereof.

7. The method of claim 6, wherein the therapeutically effective amount is effective against both a *Pseudomonas aeruginosa* bacteria and a MRSA bacteria with a MIC of not more than about 2 micrograms/mL.

\* \* \* \* \*